(12) United States Patent
Michaeli et al.

(10) Patent No.: US 12,133,761 B1
(45) Date of Patent: Nov. 5, 2024

(54) NON-INVASIVE DYNAMIC MEASUREMENT OF INTRACRANIAL RESERVE SPACE AND BRAIN ATROPHY USING CRANIAL PRESSURE

(71) Applicants: David Michaeli, Ashkelon (IL); Menashe Michaeli, Ashkelon (IL)

(72) Inventors: David Michaeli, Ashkelon (IL); Menashe Michaeli, Ashkelon (IL)

( * ) Notice: Subject to any disclaimer, the term of this patent is extended or adjusted under 35 U.S.C. 154(b) by 0 days.

(21) Appl. No.: 18/207,264

(22) Filed: Jun. 8, 2023

(51) Int. Cl.
*A61B 8/08* (2006.01)
*A61B 8/00* (2006.01)
*G01S 7/52* (2006.01)

(52) U.S. Cl.
CPC .......... *A61B 8/0816* (2013.01); *A61B 8/4444* (2013.01); *A61B 8/5207* (2013.01); *A61B 8/5223* (2013.01); *G01S 7/52038* (2013.01); *A61B 8/4281* (2013.01)

(58) Field of Classification Search
CPC ... A61B 8/0816; A61B 8/4444; A61B 8/5207; A61B 8/5223; A61B 8/4281; G01S 7/52038
See application file for complete search history.

(56) References Cited

U.S. PATENT DOCUMENTS

| | | | | |
|---|---|---|---|---|
| 10,709,345 B1* | 7/2020 | Michaeli | ................ | A61B 8/523 |
| 11,166,696 B2* | 11/2021 | Michaeli | ................ | A61B 8/429 |
| 2019/0125288 A1* | 5/2019 | Ethell | .................. | A61B 5/7282 |

* cited by examiner

*Primary Examiner* — Peter Luong
(74) *Attorney, Agent, or Firm* — Shlomo Horowitz; Shlomo Horowitz Patents and Intellectual Property Ltd.

(57) ABSTRACT

A system for non-invasive monitoring of an intracranial reserve space (ICRS) of a mammalian subject includes an at least two-dimensional multi-frequency ultrasound probe configured to emit and receive ultrasound waves into and from a head of the subject and to produce a signal of intracranial brain tissue pulsations, a pressure applicator mechanism, including at least one surface, configured to non-invasively apply an external pressure to a skull and a processor(s) configured to derive an intracranial brain tissue pulsation waveform and a length of a time interval ending when an amplitude has declined or when the waveform is compressed. In some embodiments, an existence of brain atrophy is determined. The location of the brain atrophy is determined by comparing the lengths of the time interval depending on the brain region (temporal, frontal, occipital, parietal) at which the intracranial reserve space is measured.

21 Claims, 15 Drawing Sheets

NON-INVASIVE DYNAMIC MEASUREMENT OF INTRACRANIAL RESERVE SPACE AND BRAIN ATROPHY USING CRANIAL PRESSURE

FIELD AND BACKGROUND OF THE INVENTION

The invention is in the field of medical diagnostic, systems, devices and methods, and more particularly, aims to dynamically and noninvasively measure the intracranial reserve space and brain atrophy of a subject using externally applied cranial pressure, including in some cases determining a location of the brain atrophy.

From the instant a patient with suspected brain injury arrives at the emergency room, a wide variety of complicated tests are obtained to help determine this damage. Clinical neurological investigations can be broadly classified in two ways: those that examine the anatomy of the brain (CAT scan and MRI) and those that examine the function of the brain (EEG, SPECT, and PET scan). Some of these are time-consuming and impractical for dynamic investigation such as repeating tests hourly or daily. While these diagnostic tools have advanced the understanding of the broad ranges of normative brain function, they disadvantageously rely on complex, expensive equipment that cannot be used continuously and near the bedside, and are available only in focal hospitals and not in peripheral medical clinics.

A CT scan, for instance, cannot be performed on a patient over and over within a period of 24 hours, or in some cases 6 hours, to determine anatomical deterioration in the brain, without subjecting the patient to dangerously mutagenic levels of radiation. It is also impractical to devote an expensive CT apparatus to repeated use on a single patient.

The "gold standard" to date for non-invasive measurement of the Intra Cranial Reserve Space (ICRS) is MRI Voxel Volumetry (MRIVV). However, MRIVV is expensive to purchase and to operate. It is also time consuming as the MRI scan is marked by hand, and cannot be used for wide clinical practices. It cannot be used repeatedly within a brief time frame such as minutes, hours, days or even a month, and cannot be used bedside. Interpretation of the results of the MRIVV usually requires a neuroradiologist to be present.

SUMMARY OF THE EMBODIMENTS

In order to measure intracranial reserve space and/or brain atrophy it would be helpful for the system or apparatus to be available wherever the subject is. For example, it would be advantageous if the apparatus is portable, is configured to be placed bedside. It is also beneficial if the system or apparatus be capable of being used repeatedly, for example within minutes or hours or days or months, and noninvasively on patients under observation for a suspected head injury or other neurological or neurosurgical condition, for example in order to ascertain whether anatomical deterioration such as brain atrophy has occurred over time. Such a system should also be accurate and not unnecessarily costly.

Applicant has discovered that the system and method of measured intracranial reserve space described in U.S. Pat. No. 11,166,696 to Applicant, which noninvasively measures the intracranial reserve space by applying pressure against the internal jugular vein, requires a precisely applied application of pressure against the jugular vein. This is, in part, because the jugular vein is situated alongside the internal carotid artery, at least in humans. Consequently, in using the system and method of U.S. Pat. No. 11,166,696, if the pressure applied were to inadvertently impact the carotid artery, the accuracy of the measurement of the intracranial space would be adversely affected. In order to avoid this problem, it is necessary when using the system and method of U.S. Pat. No. 11,166,696, to track the precise location of the pressure applied using a separate tracking device, such as an ultrasound tracking device.

Certain embodiments of the system, method and device described herein are advantageous in that they do not need this additional tracking device to maintain accuracy, thus significantly lowering the costs of the system and method. Furthermore, certain embodiments described herein are more accurate than, and can be implemented in less than time than, the system and method of U.S. Pat. No. 11,166,696. The time reduction may be about 50% in certain embodiments relative to U.S. Pat. No. 11,166,696. Certain embodiments are also more comfortable for the patient and physician. In addition, any minimal risk of harm using the system and method of U.S. Pat. No. 11,166,696 from the pressure to the jugular vein is absent in certain embodiments described herein.

THE FOLLOWING SUBSECTION SHOULD BE IGNORED FOR NOW, WHEN THE CLAIMS ARE FINALIZED IT WILL BE COMPLETED

An embodiment is a system for non-invasive monitoring of a general intracranial reserve space (ICRS) of a mammalian subject, comprising: an at least two-dimensional multi-frequency ultrasound probe configured to emit and receive ultrasound waves into and from a head of the subject and to produce a signal of intracranial brain tissue pulsations in at least a horizontal spatial and a vertical spatial dimension, the brain tissue pulsations responsive to pulses of a heart systole and/or respiration waves; a pressure applicator mechanism, including at least one surface and a manometer, configured to non-invasively apply an external pressure to a skull of the subject using the at least one surface; and one or more processors configured to
  (i) receive the signal and at least one output of the external pressure from the pressure applicator mechanism,
  (ii) derive from the signal an intracranial brain tissue pulsation waveform and determine a length of an interval that starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount relative to the amplitude at a predefined point in time or (B) the waveform is compressed so as to exhibit a predefined decline in variability, and
  (iii) output at least one of (a) the length, (b) an intracranial reserve space parameter derived from the length and (c) a suspected or determined medical condition of the subject derived from the length.

In some embodiments, the one or more processors are also configured to determine whether the length of time of the interval exceeds a threshold length of time.

In some embodiments, the one or more processors are also configured to determine from a look-up table which particular range of lengths of time of the interval the determined length of time fits into and to output a category of the particular range.

In some embodiments, the predefined amount is defined relative to an amplitude of the waveform beginning after a filling of a minimal intracranial reserve space comprising a convexital (superficial hemispheric) subarachnoid space (SHSS) and a brain basal surface subarachnoid shell space or a cerebral basal CFS cistern (CB CSF C) of the subject. In some embodiments, the predefined amount is an amount and the amount is at least 10% or the predefined amount is a range and all data points in the range are at least 10%.

In some embodiments, the amplitude at the predefined point in time is a beginning amplitude of the waveform occurring when the baseline stabilizes after the endpoint. In some embodiments, the predefined amount of the decline is an amount and the amount is at least 50% or the predefined amount is a range and all data points in the range are at least 50% of the beginning amplitude.

In some embodiments, the amplitude at the predefined point is the amplitude of the waveform before the first decline of the baseline. In some embodiments, the predefined amount of the decline is defined to be reached when the amplitude is less, by a particular percentage, than a particular amplitude, or an average amplitude, existing before the first decline of the baseline.

In some embodiments, the one or more processors are also configured to determine, from the length of the time interval, an amount or a degree of a brain atrophy of the subject. In some embodiments, the one or more processors are configured to determine the amount of the brain atrophy from a look-up table or a mathematical function correlating the length of the time interval with an amount of the brain atrophy. In some embodiments, the one or more processors are configured to determine an intracranial location of the brain atrophy. In some embodiments, the determination of the intracranial location derives from a length of the period of filling of at least one of (i) subarachnoid convexital space, (ii) brain basal surface shell space and (iii) intracerebral ventricles CSF space.

In some embodiments, the one or more processors are configured to determine an amount or percentage of brain atrophy in the basal forebrain or left or right hippocampus.

In some embodiments, the interval includes a period of filling of both a convexital hemispherical subarachnoid space, basal surface subarachnoid space and intracerebral ventricular space.

In some embodiments, the one or more processors are configured to determine a magnitude or existence of a basal forebrain atrophy and to determine/output a presymptomatic marker for Alzheimer's disease from the determination of the magnitude or existence of the basal forebrain atrophy.

In some embodiments, the variability of the waveform comprises a variability in at least one of the following: (i) an amplitude of the waveform (ii) an area under the curve of the waveform, (iii) a dominant frequency of the waveform, (iv) a multiaxial spectroscopy of the waveform and (v) a cerebral (phase inversion (polarization) shift of the waveform.

In some embodiments, the variability of the waveform comprises a variability in at least two of the following: (i) an amplitude of the waveform (ii) an area under the curve of the waveform, (iii) a dominant frequency of the waveform, (iv) a multiaxial (multidimensional) spectroscopy of the waveform and (v) a phase inversion-shift of the waveform.

In some embodiments, the at least one surface of the pressure applicator mechanism comprises multiple surfaces and each surface of the multiple surfaces is configured to convey external pressure to a single cranial location from among: frontal, temporal, parietal, occipital, infratentorial-cerebellar.

Another embodiment is a system for determining information concerning a brain atrophy of a mammalian subject, comprising: an at least two-dimensional multi-frequency ultrasound probe configured to emit and receive ultrasound waves into and from a head of the subject and to produce a signal of intracranial brain tissue pulsations in at least two of a horizontal (axial) spatial, a vertical (coronal) and a sagittal spatial dimension, the brain tissue pulsations responsive to pulses of a heart systole and/or respiration waves; a pressure applicator mechanism, including at least one surface and a manometer, configured to non-invasively apply an external pressure to at least one of the locations $L_i$ of the skull of the subject using the at least one surface; and one or more processors configured to receive the signal and at least one output of the external pressure from the pressure applicator mechanism, derive from the signal an intracranial brain tissue pulsation waveform and determine a length of an interval that starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount relative to the amplitude at a predefined point in time or (B) the waveform is compressed so as to exhibit a predefined decline in variability, and determine from the length of time of the interval a presence of and, if so, an amount or a degree of, the brain atrophy and output the determination.

In some embodiments, the at least one of the locations, $L_i$, comprises at least two of the following locations, $L_i$, of the cranium: (i) frontal, (ii) temporal, (iii) parietal, (iv) occipital, and further comprising using the one or more processors to determine the intracranial location of the brain atrophy based on which time interval (T) of the at least two of the locations, $L_i$, is longest.

In some embodiments, the determination of the intracranial location derives from a length of the period of filling of at least one of (i) a subarachnoid convexital space, (ii) a cerebral basal surface CSF shell and (iii) an intracerebral ventricular space (ICVS).

In some embodiments, the one or more processors are configured to determine an amount of brain atrophy in the basal forebrain or left hippocampus.

In some embodiments, the interval includes a period of filling of a cerebral convexital subarachnoid space, a cerebral basal surface CSF shell and an intracerebral ventricular space (ICVS).

In some embodiments, the pressure applicator mechanism is configured to apply external pressure to at least two of the following locations, $L_i$, of the cranium: (i) frontal, (ii) temporal, (iii) parietal, (iv) occipital and wherein the one or more processors is configured to determine a time interval (T) for filling each of the at least two locations, $L_i$, and to determine an intracranial location of the brain atrophy based on a longest time interval (T).

In some embodiments, the pressure applicator mechanism is configured to apply external pressure to at least two of the following locations, $L_i$, of the cranium: (i) frontal, (ii) temporal, (iii) parietal, (iv) occipital and (v) infratentorial-cerebellar, and wherein the one or more processors is configured to determine a time interval (T) for filling each of the at least two locations, $L_i$, and to determine an intracranial location of the brain atrophy based on a longest time interval (T).

A further embodiment is a method of non-invasively monitoring a general intracranial reserve space (ICRS) of a mammalian subject, comprising: using an at least two-dimensional multi-frequency ultrasound probe configured to emit and receive ultrasound waves into and from a head of the subject and to produce a signal of intracranial brain tissue pulsations in at least a horizontal spatial and a vertical spatial dimension, the brain tissue pulsations responsive to pulses of a heart systole and/or respiration waves; using a pressure applicator mechanism, including at least one surface and a manometer, to non-invasively apply an external pressure to a skull of the subject using the at least one surface; and using one or more processors to (a) receive the signal and at least one output of the external pressure from the pressure applicator mechanism, (b) derive from the signal an intracranial brain tissue pulsation waveform and determine a length of an interval that starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount relative to the amplitude at a predefined point in time or (B) the waveform is compressed so as to exhibit a predefined decline in variability, and (c) and output at least one of (i) the length, (ii) an intracranial reserve space parameter derived from the length and (iii) a suspected or determined medical condition of the subject derived from the length.

In some embodiments, the method further comprises determining, by the one or more processors, whether the length of time of the interval exceeds a threshold length of time.

In some embodiments, the method further comprises determining, by the one or more processors, from a look-up table which particular range of lengths of time of the interval the determined length of time fits into and further comprising outputting a category of the particular range.

In some embodiments, the predefined amount is defined relative to a beginning amplitude of the waveform occurring when the baseline stabilizes after the start point.

In some embodiments, the predefined amount is defined relative to an amplitude of the waveform beginning after a filling of a minimal intracranial reserve space comprising a cerebral convexital subarachnoid space and a basal surface CSF shell of the subject.

In some embodiments, wherein the predefined amount is an amount and the amount is at least 10% or the predefined amount is a range and all data points in the range are at least 10%.

In some embodiments, the amplitude at the predefined point in time is a beginning amplitude of the waveform occurring when the baseline stabilizes after the endpoint.

In some embodiments, the amplitude at the predefined point in time is the amplitude of the waveform before the first decline of the baseline. In some embodiments, the predefined amount of the decline is defined to be reached when the amplitude is less than, by a particular percentage, a particular amplitude, or an average amplitude, existing before the first decline of the baseline.

In some embodiments, the one or more processors are also configured to determine, from the length of the time interval, an amount or a degree of a brain atrophy of the subject. In some embodiments, the one or more processors are configured to determine the amount of the brain atrophy from a look-up table or a mathematical function correlating the length of the time interval with an amount of the brain atrophy. In some embodiments, the one or more processors are configured to determine an intracranial location of the brain atrophy. In some embodiments, the determination of the intracranial location derives from a length of the period of filling of at least one of (i) a convexital subarachnoid space, (ii) a cerebral basal surface CSF shell space and (iii) intracerebral ventricular CSF space.

In some embodiments, the one or more processors are configured to determine an amount of brain atrophy in a basal forebrain or in a left and right hippocampus.

In some embodiments, the interval includes a period of filling of both a cerebral convexital subarachnoid space, a basal surface CSF shell space, cerebral basal cisterns and intracerebral ventricular spaces (ICVS).

In some embodiments, the one or more processors are configured to determine a magnitude or existence of a basal forebrain atrophy and to determine/output a presymptomatic marker for Alzheimer's disease from the determination of a degree or existence of the basal forebrain atrophy.

A still further embodiments is a method of non-invasively determining a location of a subject's brain atrophy, comprising: using an ultrasound probe to emit and receive ultrasound waves into and from the subject's cranium and to produce a signal of intracranial brain tissue pulsations for a particular brain location; applying external pressure using at least one surface to at least one of the following locations, $L_i$, of the cranium: (i) frontal, (ii) temporal, (iii) parietal, (iv) occipital; using one or more processors to derive from the signal an intracranial brain tissue pulsation waveform and to determine a length of a time interval (T) of filling of an intracranial space at each of the at least one of the locations, $L_i$; using the one or more processors to determine an intracranial location of the brain atrophy; and outputting a determination and/or a suspicion of the location of the subject's brain atrophy.

In some embodiments, the at least one of the locations, $L_i$, comprises at least two of the locations, $L_i$, and further comprising using the one or more processors to determine the intracranial location of the brain atrophy based on which time interval (T) of the at least two of the locations, $L_i$, is longest. In some embodiments, the method further comprises applying external pressure to the cranium to at least three of the following locations, $L_i$, of the cranium: (i) frontal, (ii) temporal, (iii) parietal, (iv) occipital, using the one or more processors to determine (A) the length of the time interval (T) of filling of the intracranial space at each of the at least three of the locations, $L_i$ and (B) the intracranial location of the brain atrophy based on which time interval (T) of the at least three of the locations, $L_i$, is longest.

In some embodiments, the method further comprises using the one or more processors to determine the time interval (T) such that the time interval starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount or (B) the waveform is compressed so as to exhibit a predefined decline in variability.

These and other features, aspects and advantages will become better understood with reference to the following drawings, descriptions and claims.

BRIEF DESCRIPTION OF THE DRAWINGS

Various embodiments are herein described, by way of example only, with reference to the accompanying drawings, wherein:

FIG. 1Ca is a schematic view of an alternative embodiment for utilizing springs with piezoelectric crystals for the distal end of an ultrasound probe, in accordance with one embodiment;

DETAILED DESCRIPTION OF THE EMBODIMENTS

Figure 1A:
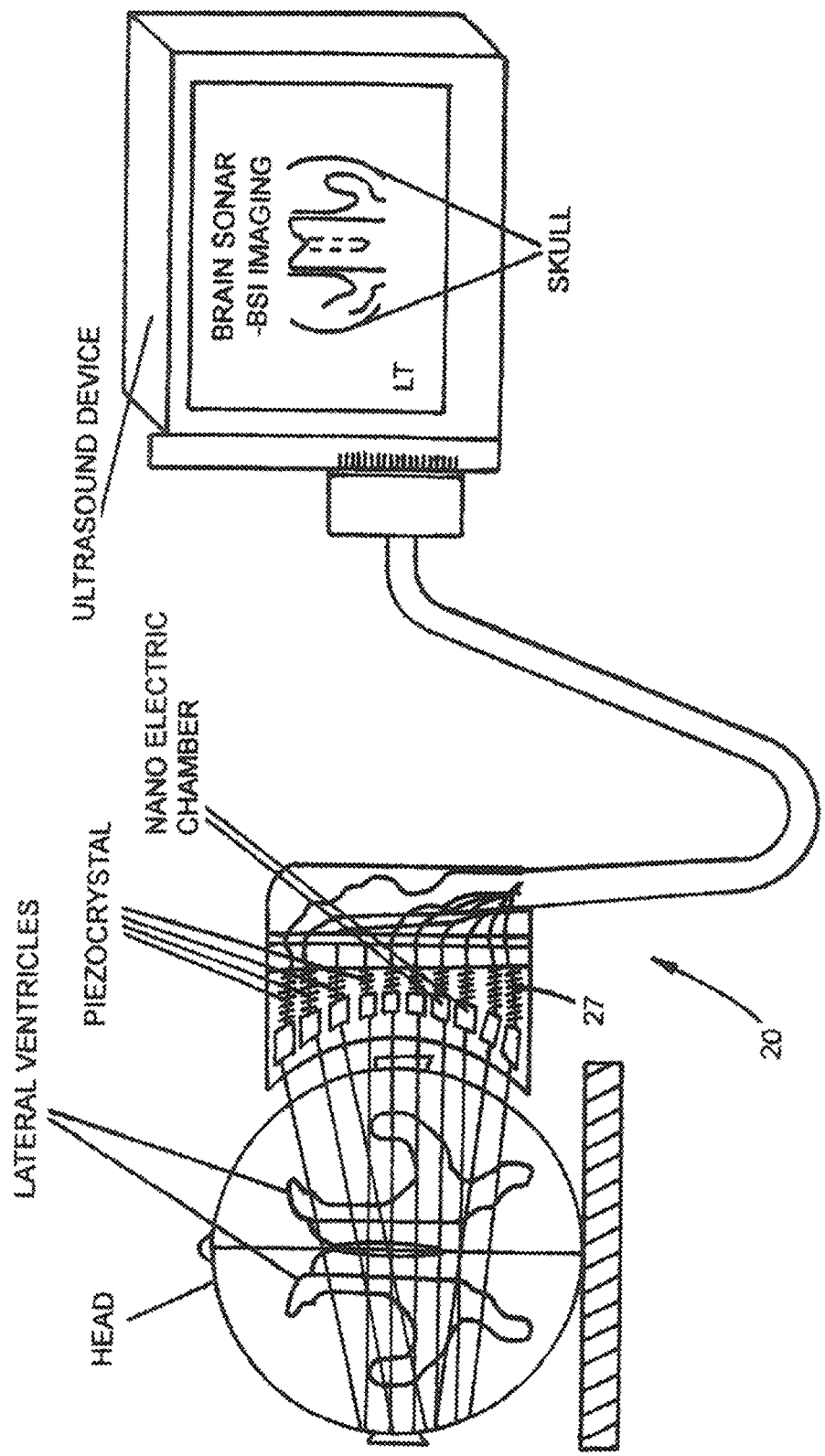
FIG. 1A is a vertical side view of an ultrasound probe, in accordance with one embodiment.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Intracranial reserve space is an anatomical phenomenon describing the volume of intracranial space filled with cerebral spinal fluid (CSF). As used in this patent application, the term "intracranial reserve space" or "ICRS" or "general intracranial reserve space" refers to all spaces within the cranium that would normally be filled with cerebral spinal fluid when the subject is healthy. This includes convexital ICRS, brain's basal surface ICRS, including basal cisterns and intracerebral ICRS, i.e. brain's ventricles (i.e., a cerebral convexital subarachnoid space, a basal surface CSF shell space, cerebral basal cisterns and intracerebral ventricular spaces (ICVS)). ICRS is therefore not limited to the convexital surface and subarachnoid space around the brain, but also includes the ventricles, cisterns and sulci that the CSF normally fills when the patient is healthy.

However, the ICRS capacity as used herein is not the actual true volume of the total ICRS as defined above but is rather merely the available capacity of the ICRS until the ICRS is deemed "occupied", for example as a result of a predefined amplitude reduction or a predefined compression of the ICP waveform (or a characteristic thereof) after applying external cranial pressure or for example due to an abnormality such as a SOL (space occupying lesion). The ICRS is deemed "occupied" by the claimed invention when the ICP waveform amplitude (or other selected variability parameter of the ICP waveform) compress to the point of being flattened, as defined by predefined quantity. It is noted that although the CSF inside the ICRS is a liquid and as such is incompressible, the "occupying" of the ICRS by a SOL, causes the CSF to be "pushed out" of the ICRS and to exit the cranium into the spinal canal. However, due to the space limitations of the spinal canal, only a small portion, approximately 5-10 cc out of 70-80 cc, of the CSF exits into the spinal canal before the ICRS is considered "occupied" and the amplitude or other variability indicator of the ICP waves flatten. Accordingly, the "ICRS capacity" as used herein is not the actual true volume of the total ICRS but is rather merely the available capacity of the ICRS before the variability parameter such as amplitude of the ICP waves decline by a predefined amount quantitatively and the ICRS is therefore deemed "occupied". In one version, the ICRS is deemed "occupied" when the ICP wave amplitude (or other selected variability parameter of the ICP waves) compress to the point of being flattened (as defined by the user quantitatively, or in other embodiments visually).

Certain embodiments generally provides a portable inexpensive device/system and method configured to noninvasively measure, in some embodiments to non-invasively measure repeatedly, both brain atrophy and an ICRS parameter such as the time to occupy the ICRS or the volume capacity of the ICRS by examining the brain tissue multi-dimensional pulsations or pulsatile activity noninvasively using ultrasound waves. The device is highly accurate and has high resolution.

It is believed that soft tissues and fluid compartments in the brain exhibit "tissue pulsations" or "tissue pulsatile activity" by exhibiting their own characteristic resonant responses to heart systolic and respiration waves (or arterial pressure pulses) radiating through the tissues of the body (input signal). When a target brain tissue is stimulated by specific ultrasound signals, the nature of the reflected ultrasound energy waves that bounce back from the tissue depends on the resonant state of the tissue (output signal). However, the brain tissue when referring to "tissue" pulsation also includes the brain's arteries, veins, cerebral magistral, venous vessels-superior and inferior sagittal sinuses. The pulsatile pattern of resonance responses of a brain tissue to specific ultrasonic stimulation is then collected and interpreted through specific mathematical algorithms to provide information about the physiological properties of the tissue. The device, method and system provides a dynamic high accuracy and high resolution technique for intracranial reserve space parameter measurement in some embodiments using ultrasound pulsatility and a skull shape adjustable ultrasonic dual frequency probes, for example needle-like dimensional array of piezocrystals lying on a rectangle strip shape and operating on different, relatively low, transmitting frequency and receiving frequency mode. Reflected ultrasonic energy is converted accurately to signals providing data corresponding to noninvasive dynamic, multiaxial pulsatility activity, intracranial reserve space and in some embodiments intracranial pressure (ICP) in the preselected volume of tissue.

Brain atrophy may be the result of age or it may be the result of disease. Although brain atrophy is not currently curable, Applicant believes that it is possible to inhibit brain atrophy with treatment. The treatments in some cases involve providing certain fluids into the brain such as water plus other components. One would define how much water is needed to provide (and provide it so as to penetrate the blood brain barrier which is a membrane, for example by providing it via a monomolecular layer) and inject the fluid to restore volume. The fluids may include at least one of vitamins, neural growth factor, anti-oxidants or growth hormones. However, if the brain atrophy exceeds 30% of the whole brain volume, these particular treatments are not thought to be successful in inhibiting brain atrophy. Therefore, a noninvasive method/system to continuously monitor an existence of and a level of brain atrophy makes it much more likely to catch it in time to take remedial action before it is too late. Obviously, then, this is a very valuable medical tool and a medical advance in itself Furthermore, each condition that causes brain atrophy is treated differently. For example, traumatic brain injury may be treated with surgery, stroke may be treated with anticlotting medication such as tissue plasminogen activator, and if the cause is a particular disease such as Alzheimer's, the treatment would be entirely different. In addition, the treatment may be different depending on the location of the brain atrophy. It is therefore important to know the location of the brain atrophy within the brain.

As seen from FIGS. 4A-4E, certain embodiments utilize a pressure application mechanism 30 that is configured to apply external pressure to at least two of the following locations, $L_i$, of the cranium: (i) frontal, (ii) temporal, (iii) parietal, (iv) occipital.

The one or more processors 52 may also be configured to determine a time interval (T) of the filling of intracranial spaces at each of the at least two locations, $L_i$, and to determine an intracranial location of the brain atrophy. This is based on determine the time interval (T) of filling of intracranial spaces for each of at least two of the locations, $L_i$, and comparing the intervals to see which is the longest. The location of the brain atrophy is determined to be the location, $L_i$, whose time interval (T) (of filling of intracranial spaces) is the longest. (separate claim for infratentorial-cerebellar). In one non-limiting implementation, the pressure application mechanism 30 is configured to apply pressure to multiple cranial locations by utilizing multiple surfaces or by being able to situate the at least one surface adjacent each of the (i) frontal, (ii) temporal, (iii) parietal, (iv) occipital portions of the cranium. In this way, a determination is made by one or more processors as to not only the existence and degree of the brain atrophy but also the location of any brain atrophy within the patient's brain.

Some non-limiting advantages of certain embodiments herein include its high resolution and accuracy, being portable, noninvasive, dynamic (i.e. can be repeated within relatively short time intervals such as an hour or even 10 minutes or less), inexpensive, and utilizing easy to operate instruments. It has the ability to measure brain atrophy and the intracranial reserve space and determine quantitatively the physiological status of any brain tissues or fluid compartments even before elevation of the ICP level occurs in some embodiments. Thus, determination of ICRS (for example, determination that ICRS has been reduced) is useful as a preventive measure and allows new additional and recurrent investigation of patient and preventive treatments. Additional modalities are available for degree of occupation ICRS and prevention of future ICP elevation. Certain embodiments detect a significant change, for example loss, of capacity (volume) of the intracranial reserve space (ICRS) ("ICRS capacity"), which is most commonly seen from swelling or a growth associated with a contusion, a cranial tumor or a stroke. If these conditions are left unchecked, they may be fatal. A loss of ICRS volume can occur within minutes or hours.

Further, spectral data (i.e. ultrasound cerebral pulsatile spectroscopy-USCPS) can be easily obtained to provide additional information on the tissue composition and structure. The versatility of certain embodiments of the invention allows it to be used to aid in diagnosis and provide information to direct the most appropriate course of therapy such as in unilateral traumatic contusions, intracranial hemorrhages, brain tumors, cerebral vascular accidents (CVAs), etc.

In a broad embodiment, certain embodiments of the invention area medical diagnostic tool based on ultrasound waves that has the capability to generate important diagnostic information non-invasively and dynamically about the physiological status of virtually any fluid space, tissue, or organ of interest tissues anywhere in the body including within the brain volume, intra-abdominal pressure (IAP), and intra-urinary bladder pressure (IUBP). Prior art methods for ultrasonic viewing of human tissue, typically utilize ultrasound pulses of one dimension, which are limited in the ultrasound intensity (allowable by government regulation) to be approximately 120 mW per $cm^2$. This was thought to be the only appropriate ultrasonic properties for penetrating the skull, and it was thought that two dimensional ultrasound could not penetrate the adult human skull due to considerable ultrasound power attenuation at the high frequencies (over 3 MHZ).

In contrast, certain embodiments now suggest use of two or three dimensional ultrasound, which can be used to penetrate the skull for example at the intensity of 40-100 MiliW/per cm$^2$, which is an FDA regulatory requirement for intensity. The three-dimensional pulsations of brain tissue that are output in certain embodiments of the invention improve over the imaging of U.S. Pat. No. 6,328,694 by one of the present inventors also in that the imaging in the '694 patent is derived from only vertical pulsatility, whereas in these embodiments the tissue pulsatility is generated from each multi-axial direction, including in some embodiments even oblique directions. This provides more data and more accurate imaging.

In still further contrast to the prior art, in some embodiments, as a result of use of dual frequencies of the ultrasound probe 20 applied to the head, so that in transmission mode the emitter uses a lower frequency and the receiver uses a higher frequency, one obtains greater depth of penetration of the ultrasound waves. In addition, this reduces black noise and improves ultrasound spatial and image resolution and quality. This transmission mode (parallel, continuous mode of the ultrasound beam) of ultrasound investigation causes activation of different anatomical targets of brain and these activated targets generate new multi-frequency intracranial ultrasound beams which are distributed in multiple directions within the intracranial cavity. The reflected beams and integrative recordings and stratification of the two different kinds of beams achieve much better image quality, elevated coefficient signal/noise ratio and improved quality of resolution and imaging. Specifically, this achieves receipt of much clearer images of the brain for evaluating the brain's midline shift and the size of brain ventricles and this provides better temporal resolution of multiaxial brain pulsatility and spectral analysis. In further contrast to the prior art, for example transcranial Doppler (TCD), which requires, and is dependent on, the expertise of the operator who operates the system, and in contrast to other prior art methods and devices requiring significant experience to interpret the results, the claimed invention is not dependent on such operator expertise and consequently the accuracy of the resulting measurements is not dependent on the operator's expertise, once the operator has been trained to use the systems or methods described herein. For example, determination of the compression of the ICP waveform to a predefined degree Can in some embodiments be determined by the computer system using software such as special purpose software. In further contrast to the prior art such as TCD and other prior art methods, which depend on the professional evaluation of the results and/or require complicated algorithms to interpret the results, the claimed invention is not dependent on professional evaluation of the results.

Even if in certain embodiments one utilizes a visual observance by the user that the variability of the amplitude of the ICP waveform has flattened, that is a clear visual determination that the operator can make quickly without extensive interpretation. In further contrast to the prior art methods and devices for measuring and monitoring the ICRS, such as MRI and CT, which require large and expensive equipment in a hospital or clinic, certain embodiments herein comprise a portable bedside apparatus that non-invasively and dynamically measures and monitors the intracranial reserve space (ICRS) of a patient, and in a typical case, a technician or nurse or even a layman can be trained to use it. In some embodiments this training can be completed in several hours.

For a suspected head injury, certain embodiments are able to detect a significant loss of volume of the ICRS for example from swelling associated with a contusion, a cranial tumor or a stroke, which if left unchecked may be fatal. Occupation of the patient's ICRS volume can occur within minutes. Monitoring ICRS and ICP in ER rooms may well dramatically improve neurosurgery by allowing earlier detection and diagnosis of space occupying lesions. In certain embodiments, certain embodiments of the invention are also helpful in treatment of other neurological conditions including stroke, brain tumors, impaired consciousness, hydrocephalus, central nervous system diseases and intracranial injury. Knowing the ICRS and ICP non-invasively and dynamically is useful to determining the course of treatment for numerous conditions of the brain and head. For example, different treatments are provided to patients with elevated ICP than patients with lower ICP.

In still further contrast to prior art methods of measuring ICRS, which require a neuroradiologist to be present personally, the method and device of certain embodiments can be implemented by a technician or others trained in its use. In further contrast to prior art non-invasive methods, which cannot be used dynamically, certain embodiments of the invention can be used dynamically, i.e. repeated within days, hours or even minutes. This means the measurements can be repeated after a relatively short amount of time, much shorter than for a brain MRI (or for a brain CT). Dynamic, non-invasive monitoring of ICRS parameters (such as the length of time it takes for the ICRS to become "occupied" or the available volume or capacity of the ICRS) opens up the possibility of treating patients before ICP elevation or clinical deterioration occurs and in some cases before 80% occupation of ICRS occurs. MRI, for example, is not available to be used dynamically (repeated use during short intervals of minutes or hours or days), and is expensive and time consuming. MRI and CT cannot be used continually or be available near the bedside, and are available only in focal hospitals and not in peripheral medical clinics. Due to these disadvantages, CT and MRI are impractical for wide clinical use for noninvasive measurement and dynamical monitoring of ICRS parameters. A CT scan is also too dangerous for repeated use. Today, not everyone who needs an MRI receives it. But if ICRS monitoring already pointed to a reduced or an elevated ICP, the MRI or CT would be justifiably given and treatment could be advanced. If even a patient with a headache were shown to have a much smaller than expected ICRS, a CT or MRI would be run and if it showed a SOL growth, emergency surgery could be considered. This could allow surgery at an earlier stage prior to clinical deterioration thus improving the expected outcome of neurosurgical interventions, which is highly dependent on the health of the patient.

If a patient has a brain hematoma, there may be no clinical symptoms yet. The intracranial pressure may even not be elevated yet. There may be a determination that the time interval (for example from an endpoint of a first decline of a baseline of the ICP waveform occurring after the external pressure is applied, the endpoint adjacent a sharp upturn of the baseline during the interval, the interval ending when either (A) an amplitude of the waveform has declined by a predefined amount (for example relative to the amplitude at a predefined point in time) or (B) the waveform is compressed so as to exhibit a predefined decline in variability) is shorter than normal for a patient that age or significantly shorter (by a predefined amount) than the actual patient's base reference ICRS time interval that had been measured earlier. If so, the physician may use this determination as a basis to promptly send the patient for a CT. If the CT results indicate that the hematoma is larger than it was the last time the CT was done, then immediate surgery may be performed to remove the hematoma before the patient is comatose. Once comatose, the likelihood of a successful outcome from a surgical removal of the hematoma is much lower than if the surgery proceeds before the patient is comatose, and especially much lower compared to a surgery that proceeds prior to the development of clinical symptoms.

Regarding use of the length for the time interval (T) as a justification for sending the patient for a CT, it is important to appreciate the fact that radiologists often oppose performing a CT in many cases in which the treating physician such a neurosurgeon recommends a CT. Thus, having the additional information that the patient's intracranial reserve space (ICRS) time interval (T) is shorter than normal for a patient that age or significantly shorter (by a predefined amount) than the actual patient's base reference ICRS time interval that had been measured earlier, is critical to overcoming the radiologists' resistance to performing the CT.

If a patient has a Space Occupying Lesion (SOL), such as an intracerebral hemorrhage (ICH), a brain tumor, a brain contusion or brain swelling, these lesions do not immediately result in an elevated intracranial pressure (ICP). For example, a space occupying lesion (SOL) may progress through multiple stages as follows: during the first stage, the lesion begins occupying the nearest convexital ICRS. Further growth of the SOL during a 2nd stage may cause depression of the walls of the ventricles of the brain experience and ventricular asymmetry. The 3rd stage is depression of basal cisterns. The fourth stage is a shift of 2 to 5 mm in the brain's midline, called BMLS. The fifth stage is a BMLS of 5-10 mm and the $6^{th}$ stage is a BMLS of 10-15 mm or more.

It is important to note that during the first four stages of the growth of a space occupying lesion (SOL), clinical signs are very difficult to obtain and symptoms of disease are very difficult to discern. Although a patient may have a large-sized SOL as a result of stages 1-4 of SOL growth, compensatory mechanisms of ICRS, namely the ICRS volume and cerebral spinal fluid (CSF) outflow from the head, may prevent clinical manifestation of signs of ICRS occupation and elevated intracranial pressure (ICP). This is especially true of elderly patients who have elevated ICRS capacity since during aging, ICRS grows due to central and peripheral brain tissue atrophy. Accordingly, dynamic evaluation of ICRS and changes in ICRS, may provide crucial information even before manifestation of ICP elevation. ICRS parameters such as the extent of reduction in the volume of ICRS, for example from a SOL, or the length of time until ICRS is occupied (as defined by variability declining by a predefined amount) during a specially defined time interval (T) after external cranial pressure is applied to the subject, are good predictors of neurological developments of the patient, before clinical deterioration, and has significant prognostic value in neurosurgery. Specifically, reduction of ICRS may well indicate that in the near future the patient will develop an elevated ICP and/or will experience clinical-neurological deterioration, something the prior art does not achieve. Consequently, ICRS monitoring may well be a more sensitive marker than ICP monitoring for patients with acute and chronic SOL growth. ICP elevation occurs after ICRS occupation and patients with ICP elevation already have experienced significant clinical deterioration requiring immediate surgical intervention. Furthermore, a significant reduction of the patient's ICRS within a short time interval is an indicator justifying recurrent CT investigation. Even without clinical-neurological deterioration, dynamic monitoring of ICRS is an important additional tool for neurologists and neurosurgeons justifying repeating a CT, even when the previous CT occurred 10-15 minutes ago, something that normally would not be allowed under CT guidelines. The repeated CT can also save previous time consumed by discussions between radiologists and other colleagues as to whether to repeat a CT.

Note that in contrast to reduction of ICRS from a first measurement to a second measurement (especially in a relatively short time interval) which may well indicate future elevated ICP or clinical deterioration, in adults, if based on a single measurement the ICRS is found to be high (based on length of time interval (T) or based on absolute ICRS capacity), this alone would indicate that intracranial pressure is likely to be low or normal and conversely, if the ICRS is found to be low (based on length of time interval (T) or based on absolute ICRS capacity) in a single measurement, it indicates that intracranial pressure is likely to be high or normal. In further contrast to prior art techniques, certain embodiments may also be useful as a general check-up for healthy individuals. For example, a CVA (stroke) is common among the elderly and can be prevented in high-risk patients or can be efficiently treated if detected in a timely manner. As a bedside noninvasive apparatus which does not involve high levels of radiation, the apparatus of the system described herein can be used to perform routine preventative screening on the elderly.

The principles and operation of a Non-Invasive Dynamic Measurement of Brain Atrophy and Intracranial Reserve Space Using Cranial Pressure according to the invention may be better understood with reference to the drawings and the accompanying description.

In this patent application, the term "intracranial brain tissue pulsation waveform" or "ICP waveform" refers to the wave function that is obtained, and in some embodiments displayed, when the signal from the ultrasound probe placed on the subject's head (in some embodiments in both a horizontal position and in a vertical position) is adapted by software 55, such as special purpose software 55, of the computer system 50 or processing unit 50 of some embodiments of the claimed invention to show real time images of brain tissue pulsation. For example, the ultrasound probe 20 provides brain pulsations, such as two-dimensional brain pulsations, that are adapted by software, i.e. in some embodiments by first applying the fast fourier transform (FFT) and then applying the inverse fast fourier transform (IFFT), to yield two-dimensional pulsatility which in some embodiments is further converted to three-dimensional pulsatility by including signals from both horizontal and vertical positions held by the probe. The additional dimensions provide more information and more accurately capture the brain tissue and its real-time movements. For example, intracranial pressure and intracranial reserve space are more precise by using both dimensions since horizontal pulsations may be more informative both for ICP and for the compression of the waveform used for ICRS. Multi-dimensionality, i.e. even further dimensions such as oblique directions, may be included utilizing computer science. Accordingly, the intracranial brain tissue pulsation waveform used in certain embodiments takes into account brain tissue pulsations and respiration waves. In some embodiments, it also takes into account cerebral spinal fluid (CSF) outflow.

"ICP waves" refers to the waves of the ICP waveform.

Referring now to FIGS. 1 through 3, there are shown an example of a system for observing ICRS in a volume of tissue in a subject in accordance with one embodiment.

Figure 2A:
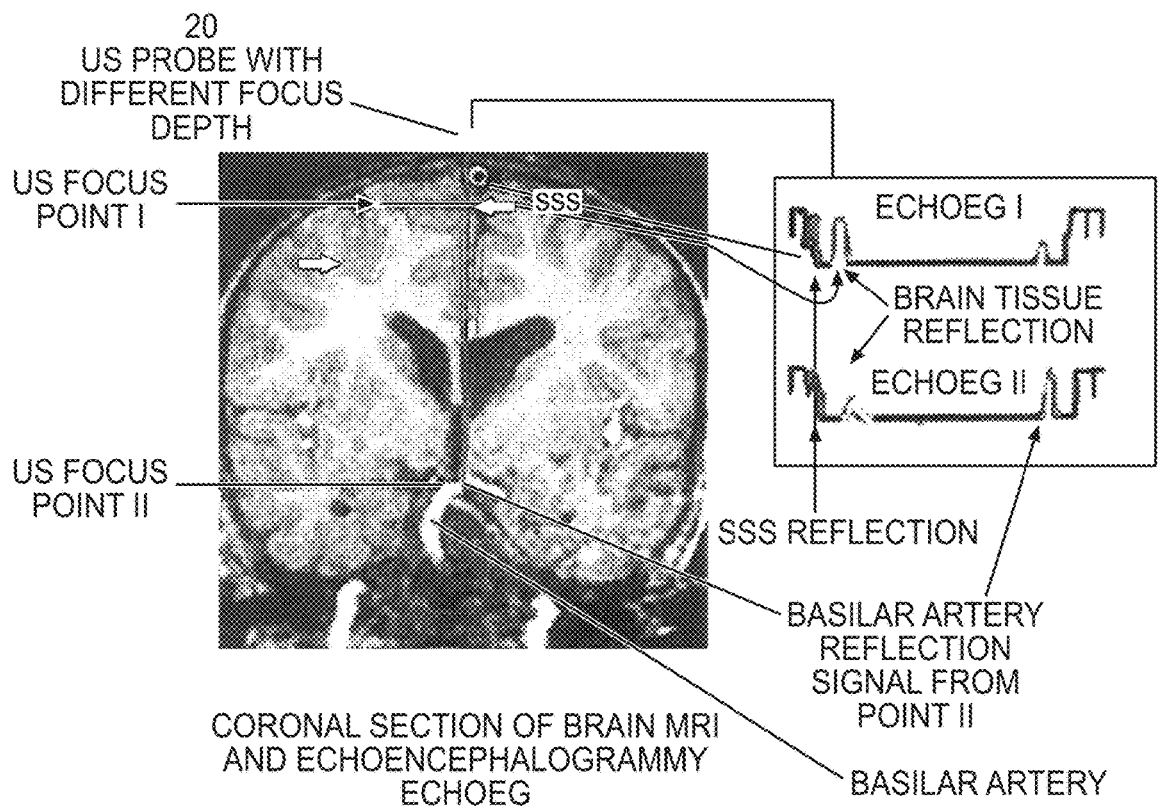
FIG. 2A is a coronal sectional view of a brain MRI and on the right an echo encephalogram showing the real-time pattern of brain pulsation from ultrasound imaging using a one-dimensional A mode ultrasound probe from which it is possible to derive ICP waveform, wherein SSS refers to Superior Sagittal Sinus, in accordance with one embodiment.

FIG. 2A shows on the left a brain MRI to help visualize where the ultrasound reflections come from. The right side of FIG. 2A shows an echo encephalogram with real-time pattern of brain pulsation from ultrasound imaging using a one-dimensional A mode ultrasound probe. It is possible using the computer system of certain embodiments of the invention to derive ICP waveform directly from the one-dimensional signal on the right of FIG. 2A. This is less expensive that a two-dimensional ultrasound probe 20. However, it is also less accurate since it is derived from a one-dimensional probe and also because it is not derived from an image.

Figure 2B:
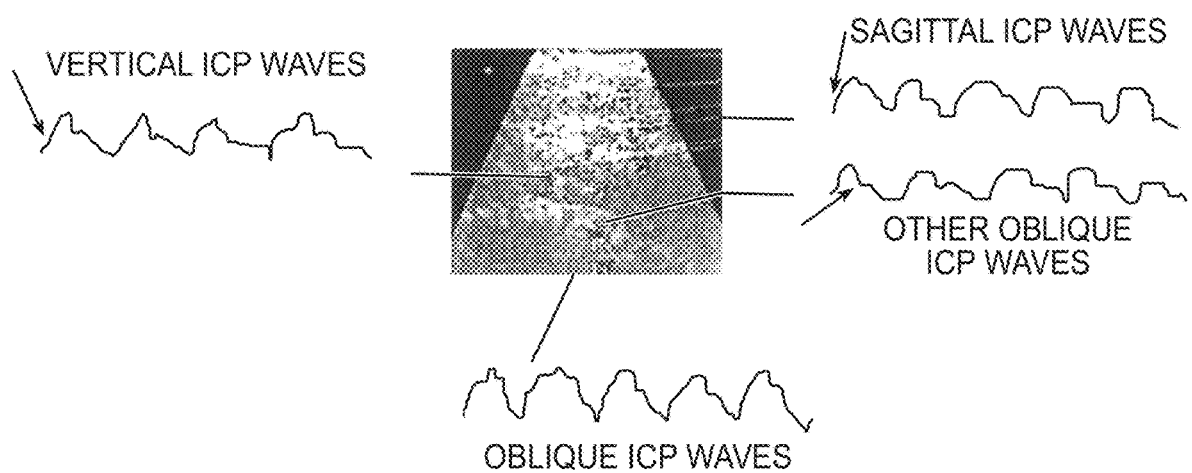
FIG. 2B is a further sectional view showing in the middle of the figure the real-time image of multi-dimensional brain tissue pulsation from two-dimensional ultrasound sector imaging and on the left and right ICP waveform derived from the image, in accordance with one embodiment.

FIG. 2B shows a sectional view in the middle of the figure having a real-time image of multi-dimensional brain tissue pulsation from a two-dimensional ultrasound sector imaging probe 20. On the left of FIG. 2B and on the right of FIG. 2B are ICP waveforms derived from the image in the middle. Although more expensive, these ICP waveforms are more accurate because they derive from an image and because they derive from a two-dimensional ultrasound probe. Both the graph on the right of FIG. 2A and the graphs on the left and right of FIG. 2B represent the reflected ultrasound energy which is detected from a selected pixel in the tissue at different depths and exhibit the pulsatile activity (differential between emitted and reflected ultrasound energy-brain tissue's ultrasound energy shift) as a function of time. As shown, some observation of pulsatile activity will vary with orientation or direction of the observations.

In a healthy individual, it takes time, for example about 3 seconds (depending upon age and other factors) for the intracranial reserve space to be occupied. In a patient with some of the ICRS already occupied by a pathological growth, the time to "occupy" the ICRS by the extra blood would be significantly less.

The time interval for occupying the ICRS during the specially defined time interval (T) that occurs after commencement of the externally applied cranial pressure is a measure of how long it takes to "occupy" the intracranial reserve space. For a normal adult, taking into consideration age and if desired other suitable factors, it takes about 3 seconds to "occupy" the intracranial reserve space after mild external cranial pressure is applied. If the subject's intracranial reserve space instead took only one second to become "occupied", for example, it could indicate growth of an SOL within the cranium that had reduced the volume of the ICRS already before the externally applied pressure was applied. If on the other hand it took too long, for example 7 seconds, that could indicate that the intracranial reserve space was too large. If it took 2 seconds for the ICRS to become "occupied", the measurement is repeated, at least according to one embodiment. If the ICRS is found to be constant based on receiving similar results from multiple measurements, then if the deviation from 3 seconds is small enough, for example 2 seconds or 4 seconds, then the subject may be considered to not be in danger. This conclusion is only one non-limiting example of a medical conclusion that may be made from the additional useful information provided by certain embodiments herein.

Figure 3A:
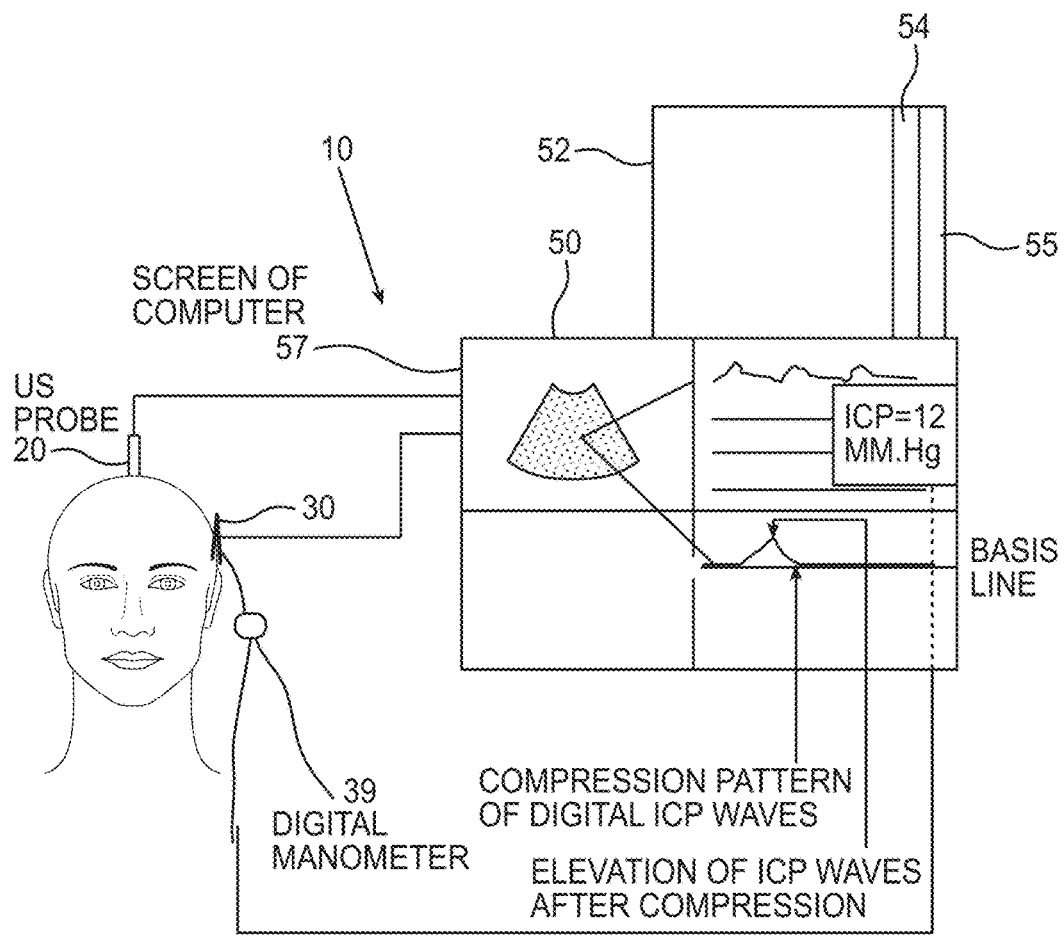
FIG. 3A is a schematic view of a system for noninvasive ICRS and ICP monitoring, in accordance with one embodiment.

Referring now to FIG. 3A, there is shown a non-invasive measurement of the ICP as well as non-invasive measurement of amplitude of ICP waveform compression of brain tissue pulsation.

Application of cranial pressure, for example in increments such as stepwise increments (or all at once if the desired external pressure has already been determined), may be is performed for example on a patient in any position whether sitting or supine in accordance with one embodiment, under guidance of 2D-ultrasound imaging.

As shown in FIG. 3A, certain embodiments are a system for monitoring intracranial reserve space. FIG. 3A shows one embodiment of the system 10 including a display screen 57 (forming part of the computer system 50) upon which is shown side by side: pulsatile views of the cranium from the probe 20 including an externally placed cranial location marker and a compressional ICP waveform graph showing the minimal/maximal amplitude (or other waveform parameter) of the ICP waveform.

System 10 includes in some embodiments an ultrasound probe 20 for application to the cranium, an instrument 30 for applying external pressure to the cranium of the subject and a computer system or processing unit 50 for processing signals generated by the ultrasound probe 20 and for determining an intracranial reserve parameter. In some embodiments, the ICRS parameter is an ICRS capacity measuring an absolute volume from application of external cranial pressure during a time interval ending when the ICP waveform compresses to a predefined extent as measured by a decline in its variability. In other embodiments, the ICRS parameter is a length of time determined by a calculation made by the computer system 50.

In certain embodiments, system 10 for non-invasive monitoring of an intracranial reserve space (ICRS) parameter of a mammalian subject, comprises an ultrasound probe 20, such as a multi-frequency ultrasound probe 20, that is configured, beginning at a start time, to emit and receive ultrasound waves into and from a head of the subject and to produce a signal corresponding to brain tissue pulsation. System 10 in some embodiments also includes an instrument 30 configured to non-invasively apply a pressure against the cranium.

When the external cranial pressure has been determined to have started, in some embodiments the user can push a timer. Alternatively, the computer system 50 can determine when the pressure starts and automatically start the timing function. In some embodiments, the computer system 50 simply records the time or the amount of time, such as seconds or milliseconds elapsed, throughout beginning when a specifically defined time interval (T) starts. These are non-limiting of ways of measuring the length of the time interval (T), as defined below.

In some embodiments, the processing unit determines when the time interval (T) begins not as the moment when external cranial pressure is applied but rather when the ICP waveform exhibits certain predefined characteristics. For example, the beginning of the time interval (T), in some embodiments, is defined as an endpoint of a first decline of a baseline of the waveform occurring after the external pressure is applied. That endpoint of the first decline of the baseline is recognized by the fact that it is adjacent to a sharp upturn of the baseline which upturn is included in the interval. The end of the interval is defined as when either (A) the amplitude of the waveform has declined by a predefined amount (for example relative to the amplitude at a predefined point in time) or (B) the waveform is compressed so as to exhibit a predefined decline in variability. As used herein, the term "decline" in regard to the baseline refers to the baseline dropping on the graph or image. Since a baseline is a line it cannot be said to decline in value.

In some embodiments, the predefined amount is an amount and the amount is at least 10% or the predefined amount is a range and all data points in the range are at least 10%. In some embodiments, the predefined amount is an amount and the amount is at least 20% (or at least 30% or at least 40% or at least 50%) or the predefined amount is a range and all data points in the range are at least 20% or at least 30% or at least 40% or at least 50%. In some embodiments, the predefined amount of the decline is defined to be reached when the amplitude is less, by a particular percentage, than a particular amplitude, or an average amplitude, existing before the first decline of the baseline.

Figure 6A:
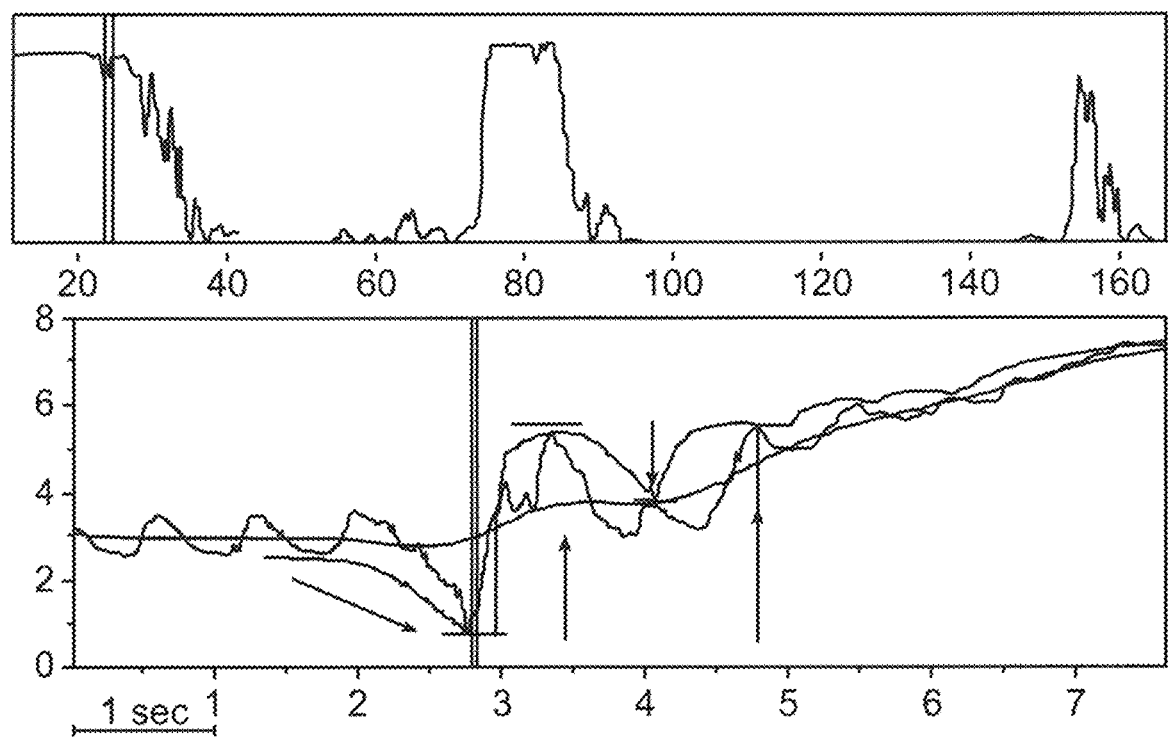
FIG. 6A is a graph of an ICP waveform with certain critical points marked off showing changes or turning points in the baseline and or amplitude reflecting the impact of the externally applied cranial pressure, in accordance with one embodiment.

FIG. 6A is a graph of an ICP waveform as the external cranial pressure is applied. In this case the cranial pressure was incrementally elevated. The graph in FIG. 6A displays certain critical junctures that are marked off to show changes or turning points in the baseline and/or the amplitude of the ICP waveform reflecting the impact of the externally applied cranial pressure. Initially, after the externally applied pressure reaches a certain strength, the amplitude of the ICP waveform initially increases and then the baseline declines markedly followed by a marked increase that begins a little before the 3 second mark. In this particular graph the baseline increased to a point higher than before its decline, although that is not a requirement. Note that "amplitude" refers to the vertical distance from the peak to the trough (or baseline).

Figure 6B:
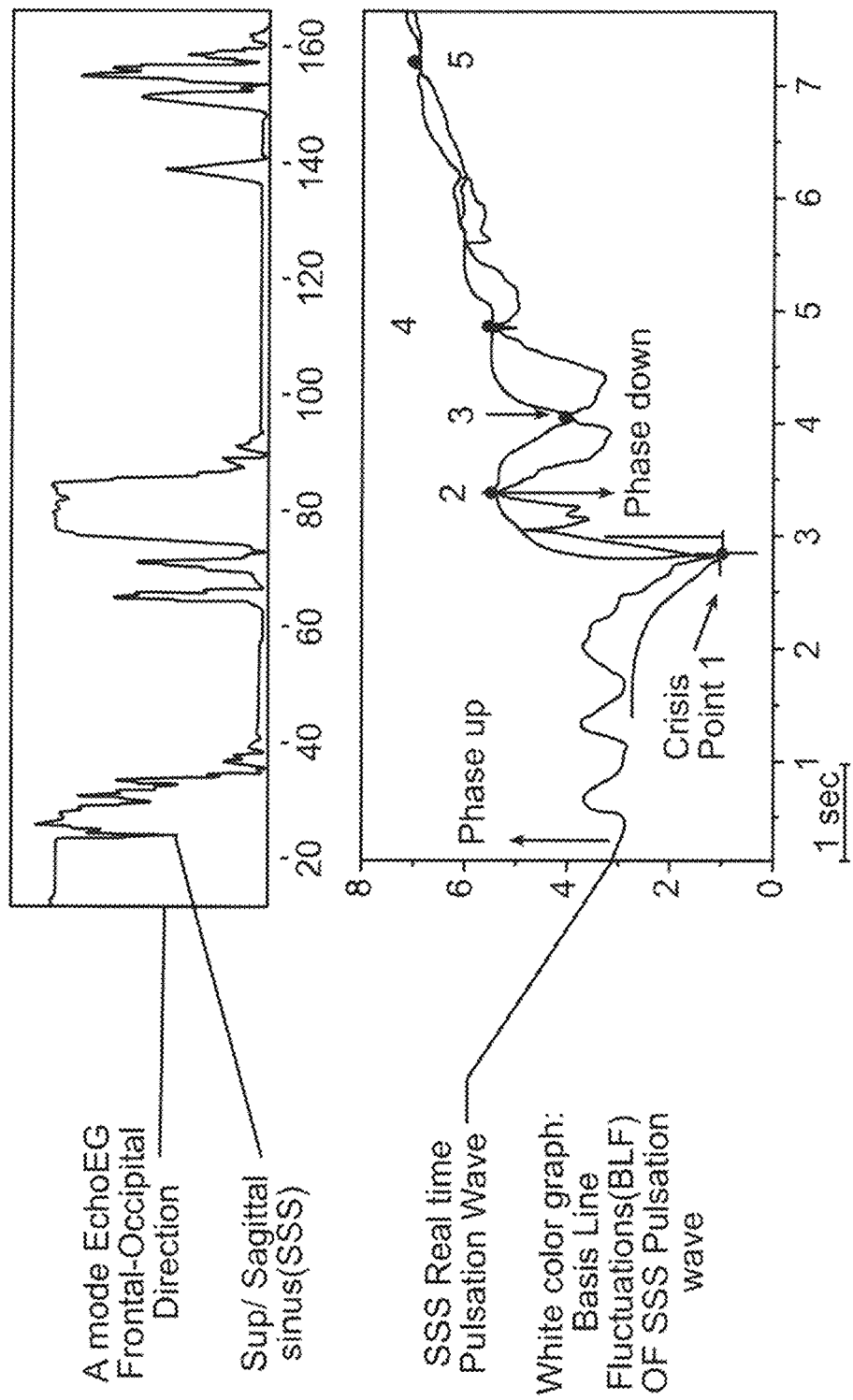
FIG. 6B is a graph of an ICP waveform with certain critical points marked off showing changes or turning points in the baseline and or amplitude, in accordance with one embodiment.
Figure 7:
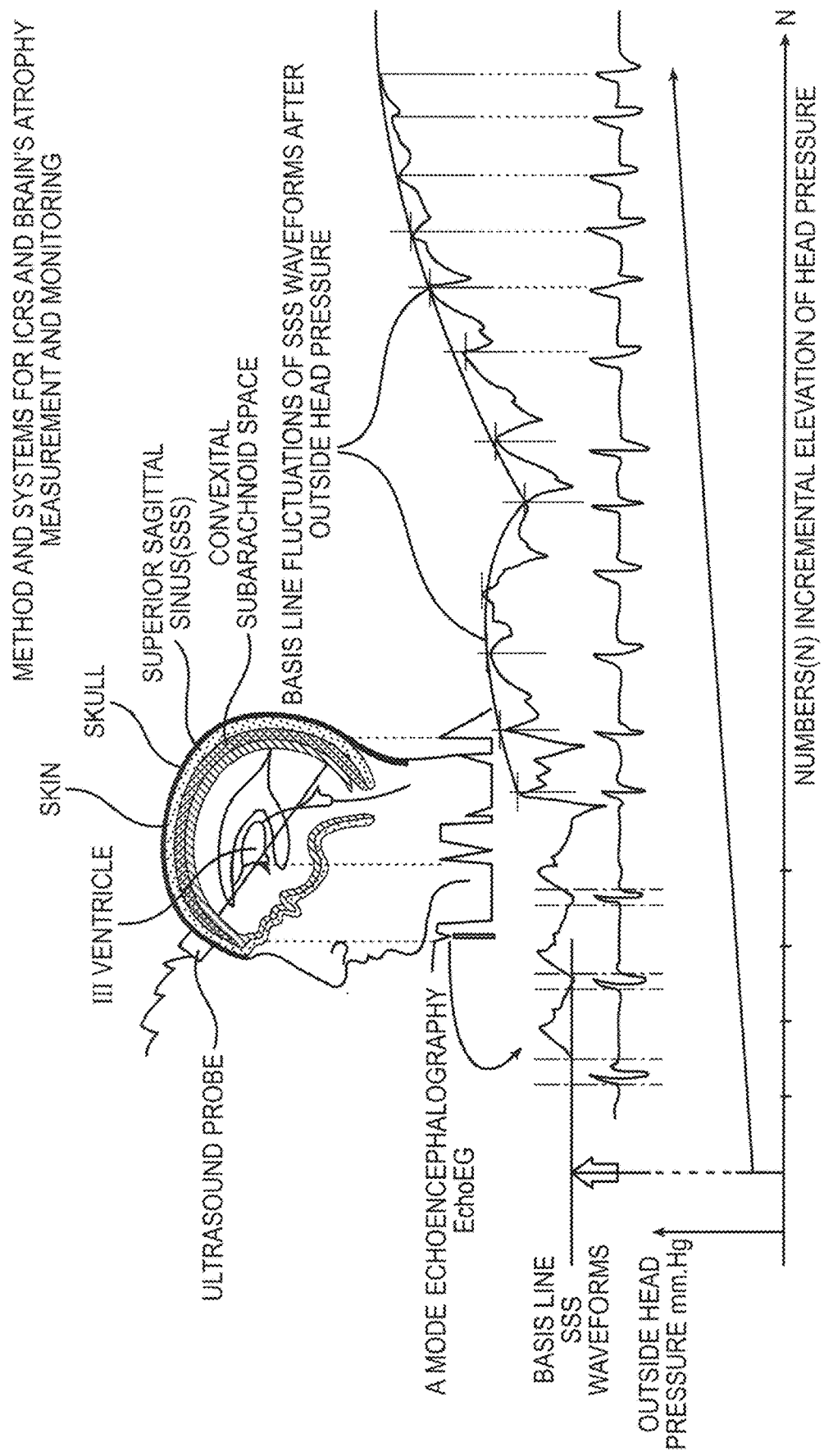
FIG. 7 is a graph of an ICP waveform showing the effect on the baseline and on the amplitude of the ICP waveform from the external cranial pressure alongside the subject's echoencephalography, in accordance with one embodiment.

In FIG. 6A and FIG. 6B, the top graph is an electrocardiogram. After each systole, in the mode called "phase up" the waveform or baseline goes up whereas in the mode called "phase down" after each systole the waveform or baseline declines; there is a short interval between phase up and phase down during which there is no real baseline and therefor no real amplitude.

Figure 5:
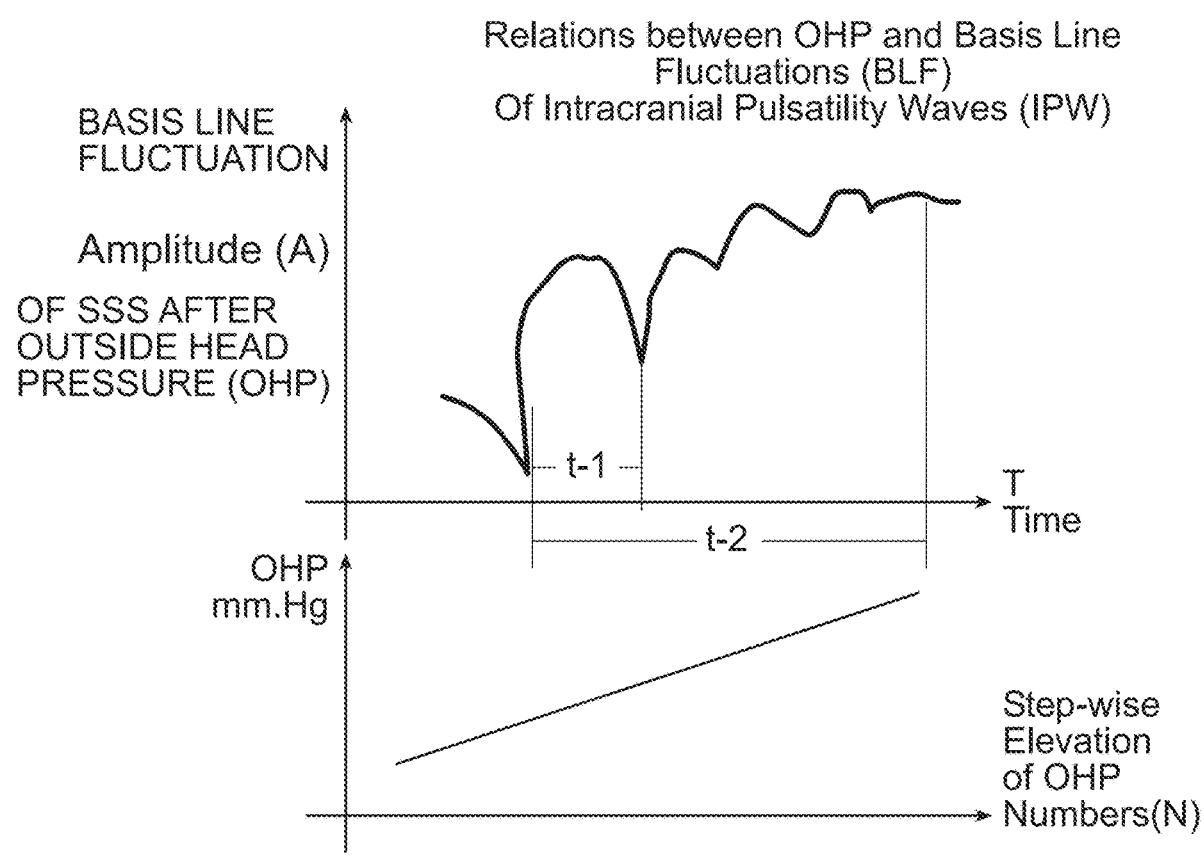
FIG. 5 is a graph of an ICP waveform showing the fluctuations of the baseline of the IP waveform from the external cranial pressure between two crisis points, in accordance with one embodiment.

In FIG. 6A, the first "crisis point"—at just prior to three seconds marked off on the x-axis of the graph on the bottom of the graph—may be considered to be the endpoint of that first decline of the baseline of the waveform occurring after the external cranial pressure is applied. It is followed by a sharp upturn in the baseline. FIG. 5 illustrates the range "t–1" between that first crisis point (as the beginning of the range "t–1") until a second crisis point at the end of that range. Range "t–1" characterizes the period in which the amplitude is disrupted.

As seen in FIG. 6A, the first decline in the baseline is understood to be the first decline in the baseline wherein such decline exceeds a predefined amount (the amount may be defined in various ways). For example, in one particular non-limiting example, at least a 5% decline. In other embodiments, at least a 10% decline, or at least a 15% or a 20% or a 25% or a 30% or a 35% or a 40% or a 45% or a 50% decline. Each is a separate embodiment.

In FIG. 6A, the period of approximately 2.0 seconds to 2.8 seconds represents the first decline in the baseline. Although the claimed invention is not limited by physiological explanations, the accepted physiological explanation for the decline in the baseline is that the external cranial pressure causes a slight decline in the diameter of the cranium. This in turn causes the cerebrospinal fluid (CSF) to exit the convexital reserve space toward the spinal cord, which causes a sharp reduction in intracranial pressure and a dropping of the baseline of the ICP waveform. However, this sharp reduction is brief because the spinal cord is only able to absorb a relatively small amount of CSF. Accordingly, once that outlet for the CSF has been fully utilized, the continued elevation, for example incremental elevation, of the externally applied cranial pressure by mechanism or instrument 30 results in sharp upturn in the baseline. That upturn is visible in FIG. 6A from about 2.8 seconds until about 3.2 seconds. The amplitude of the waveform is also higher at this point. Although the time interval (T) will end (for example at some point between 5 and 6 seconds or thereafter as shown in FIG. 6A) when either (A) an amplitude of the waveform has declined by a predefined amount (for example relative to the amplitude at a predefined point in time) or (B) the waveform is compressed so as to exhibit a predefined decline in variability, during the interlude from between 3.2 seconds and about 4.9 seconds, the normal pattern of the waveform continues to be disrupted as the external pressure keeps going up yet different portions of the intracranial spaces keep filling up. These countervailing forces produce the pattern seen in FIG. 6A from about 3.2 seconds to about 4.9 seconds (the length of this period varies from individual to individual depending on much brain atrophy the individual has).

System 10 in some embodiments also includes a computer system 50 configured with all suitable hardware and software necessary to receive the signal from the ultrasound probe 20 configured for the subject's skull 11 and to receive an output of a start time of the externally applied pressure on the cranium of the subject. Computer system 50 in some embodiments is also configured, for example using one or more processors 52 and software 55, such as special purpose software 55, and all suitable and necessary hardware and software including memory storage 54, to derive from the signal an intracranial brain tissue pulsation waveform, and to monitor time so as to determine a length of time from the start time of the time interval (T) to a subsequent time at which either (A) an amplitude of the waveform has declined by a predefined amount (for example relative to the amplitude at a predefined point in time) or (B) the waveform is sufficiently compressed so as to exhibit a predefined decline in variability. The software 55 for deriving the intracranial brain tissue pulsation waveform from the signal of the ultrasound probe 20 is known or readily adaptable from known software associated with single or two-dimensional ultrasound probes. Computer system 50 also includes in some embodiments all suitable hardware and software for displaying brain tissue pulsatility, such as the ultrasound device shown in FIG. 1A.

It should be unnecessary for the software of processing unit 50 to utilize artificial intelligence to identify the beginning point and endpoint of the time interval (T) in the graph of the ICP waveform derived from the signal obtained from the probe 20. However, if necessary artificial intelligence such as machine learning and deep neural networks can be enlisted to achieve this more efficiently by looking at the patterns of many individuals of particular ages (or other characteristics).

"Deriving" the ICP waveform from the signal of probe 20 includes deriving it directly and includes deriving the ICP waveform from the signal indirectly. In one embodiment, computer system 50 indirectly derives the ICP waveform from the signal generated by probe 20 by deriving the ICP waveform from an image of brain tissue pulsation wherein the image of brain tissue pulsation had been derived from the signal generated by probe 20. In a different embodiment, computer system 50 directly derives the ICP waveform from the signal generated by probe 20, which typically is a two-dimensional probe 20 but can also be a one-dimensional probe 20.

FIG. 6B shows an intracranial brain tissue pulsation waveform starting with a certain variability in amplitude, beginning to compress or flatten and continuing until the variability, as measured in terms of amplitude, is compressed. In some embodiments, certain portions of computer system 50 (for example one or more processors or display devices) are remote from the other parts of system 10 and connected by wired or wireless communications for example nearby but in another room of a hospital department, or in other cases more remote and in communication over the Internet. If all portions of system 10 are in one place and connected, system 10 can also be referred to as an apparatus 10 or device 10.

External pressure to the cranium applied in accordance with certain embodiments described herein in some patients initially causes an elevation of the amplitude of brain pulsation. Additional applied pressure results, in these patients, in a decrease of amplitude to a more compressed line. This external pressure causes a decrease of pulsation variability in the brain until it becomes a relative straight-line. The amount of time until this happens correlates with the magnitude of the original ICRS capacity.

To appreciate the value of certain embodiments, suppose an 80 year old falls or gets hit on the head. There may be intracranial bleeding. If the patient has a lot of brain atrophy or is generally healthy and has a lot of reserve space, the patient may not feel any abnormal symptoms including even a headache. They there may be bleeding within the cranium. This is because the blood from the bleeding is able to enter the intracranial reserve spaces which start to fill up. The patient will not yet complain about a headache. Furthermore, the intracranial pressure may not increase because the reserve space has not filled up. However, this patient's medical situation is serious.

If this patient presents himself in an emergency room setting everyone will be apt to say that he is ok and that he should be sent home since he feels no pain or headache or other symptoms. Even when the neurosurgeons check him, since he is fully conscious and feels no symptoms they will send him home. A CT will not be authorized under these circumstances (the radiologists will oppose it).

Suppose they release him, which is a commonplace occurrence in the emergency rooms of today. If the patient goes to sleep and blood continues to fill the reserve space he may lose consciousness during sleep. A family member may detect that fact as a result of the breathing sounds changing. The family then brings him back to the emergency room. At this point his intracranial pressure has increased and he is in a coma. He will probably be intubated and may even die. If the neurosurgeons operate now the morbidity risk is 50%-70% (for example because the elevated ICP destroys the brain stem).

Now suppose that instead the hospital emergency rooms are equipped with a system 10 (or using methods 100 or 200) that includes an at least two-dimensional multi-frequency ultrasound probe configured to emit and receive ultrasound waves into and from a head of the subject and to produce a signal of intracranial brain tissue pulsations, a pressure applicator mechanism, including at least one surface and a manometer, configured to non-invasively apply an external pressure to a skull of the subject using the at least one surface, and one or more processors configured to receive the signal and at least one output (at least the initial output) of the external pressure from the pressure applicator mechanism, derive from the signal an intracranial brain tissue pulsation waveform and determine a length of a time interval that starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount (for example relative to the amplitude at a predefined point in time) or (B) the waveform is compressed so as to exhibit a predefined decline in variability, and output at least one of (a) the length, (b) an intracranial reserve space parameter derived from the length and (c) a suspected or determined medical condition of the subject derived from the length.

When the 80 year old patient who fell or hit his head now first comes to the emergency room, his intracranial reserve space is measured. Then it is re-measured for example 30 minutes later. One cannot do that now invasively since on cannot measure invasively twice within such a short time. If the intracranial reserve space has contracted significantly as defined by a predefined absolute or a predefined relative amount or percentage, he will not be released because it is possible to conclude that there is a brain swelling or intracranial bleeding. In such a case a CT will in fact be authorized even though the intracranial pressure is not elevated and there are no symptoms. Now if the CT shows a hemorrhage or something else serious the neurosurgeons can operate knowing that the surgery will have a much lower chance of morbidity (since the ICP is not elevated).

Similarly, in a case where a patient is checked (with no head injury and no fall) and there is no information (no MRI and no CT), using certain embodiments of system 10 or methods 100, 200, the patient's intracranial reserve space is checked. If it is too high (i.e. it takes too long to fill the intracranial reserve space) and he feels fine we can conclude that there is brain atrophy (FIG. 8) and request an MRI or CT or other imaging modality. This could indicate the beginning of Alzheimer's disease or a lack of blood flow to certain parts of the brain. The ICRS can be measured dynamically and compared from one check-up to another (for example every 6 months or a year). If after a year the brain atrophy continues to increase then a CT will be authorized, whereas today, a CT would not be authorized without symptoms.

While the amplitude of the ICP waveform has been discussed so far, this is not the only measure of ICP waveform variability useful for certain embodiments of the system or the system or methods described herein. In one embodiment, variability of the intracranial brain tissue pulsation waveform comprises at least one of the following ICP waveform parameters: (i) a variability of an amplitude of the waveform and (ii) a variability of an area under the curve of the waveform, (iii) a variability of a dominant frequency of the waveform (for example a frequency between 0.1 and 35 MHZ), (iv) a direction of high frequency shift (for example of between 12 and 35 MHZ) of the waveform (which affects the amplitude and hence variability of the waveform), (v) a phase shift of the waveform (which affects the amplitude, and hence variability, of the waveform and (vi) a variability of a multiaxial spectroscopy of the waveform (ICPWMS). In another embodiment, variability of the intracranial brain tissue pulsation waveform comprises a variability of at least one of the following ICP waveform parameters: (i) an amplitude of the waveform, (ii) an area under the curve of the waveform, (iii) a dominant frequency of the waveform (for example a frequency between 0.1 and 35 MHz) and (iv) a multiaxial spectroscopy of the waveform (ICPWMS). The spectroscopy referred to herein is a mechanical motion (pulsatility) spectroscopy, not a magnetic or electrical spectroscopy. Other functions that quantify variability of the ICP waveform are also within certain embodiments of the system or methods described herein, including but not necessarily limited to combinations and/or derivatives of the above six examples of ICP waveform variability indicia/parameters.

In order to determine if the amplitude or other characteristic of the intracranial brain tissue pulsation waveform has reached a predefined decline in variability, for example as shown in FIG. 6B, according to one embodiment, a comparison of variability during a predefined period of time is made with a previous variability during a preceding period of time and this is performed by one or more processors of the computer system 50, in accordance with special purpose software. Variability is defined, according to one option, by the difference between the highest and lowest amplitude (or other waveform variability characteristic) during a certain period or cycle. For example, the predefined decline in ICP waveform variability is defined such that variability of an amplitude (or of other waveform parameter indicative of variability) of the waveform during the predefined period of time is ten percent (or in other embodiments 5%, 15%, 20%, 30%, 40%, 50%, 60%, 70%, 80% or 90%) or is no more than ten percent (or in other embodiments no more than 5%, 15%, 20%, 30%, 40%, 50%, 60%, 70%, 80% or 90%) of a variability during a previous period of time of predetermined length. In other words, the waveform has compressed to such an extent that its variability is only 10% of what it previously was, for example during a previous cycle. In one example, the predefined decline in variability of the waveform is defined such that the waveform has compressed 80% such that its variability has become only 20% of what its variability was during some previous measurement.

In some embodiments the "previous measurement" of its variability that the comparison is made against is the variability of the waveform during a previous cycle, or in other embodiments during an average of certain previous cycles such as an average of the variability during the preceding 2 cycles, or during the preceding 3 cycles, or during the preceding X cycles, wherein X can be any positive integer.

In another example, the predefined decline in variability is defined such that once the decline in variability has persisted for at least a certain amount of time or at least a certain number of predefined periods of time or cycles, only then is it counted as having achieved the required decline in variability. Since the predefined decline in variability is quantified, according to one embodiment, the computer system signals that the interval end time has been reached, thereby triggering the computer system to calculate the time interval, which represents how long it took for the ICRS to become "occupied".

Figure 4A:
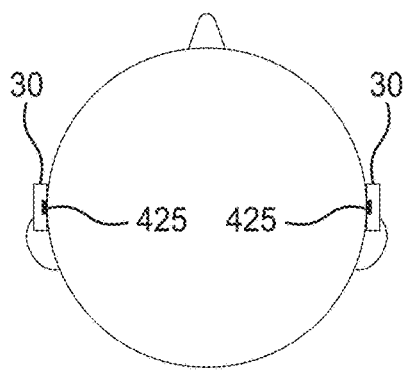
FIG. 4A is a top view of a pressure applying mechanism applying pressure against the cranium temporally, in accordance with one embodiment.
Figure 4B:
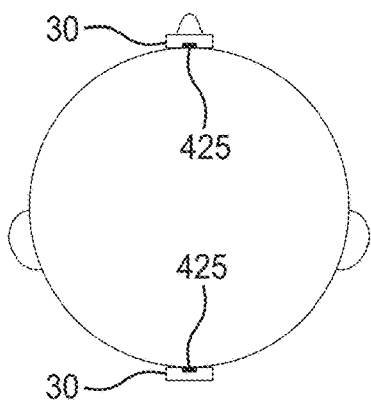
FIG. 4B is a top view of a pressure applying mechanism applying pressure against the cranium frontally and occipitally, in accordance with one embodiment.
Figure 4C:
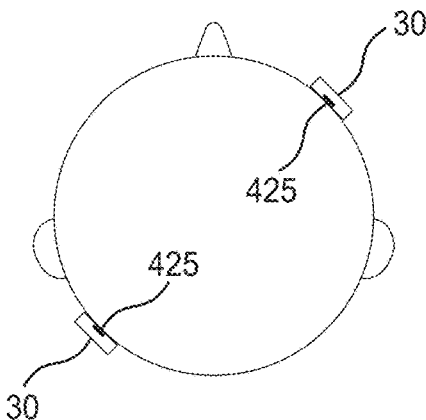
FIG. 4C is a top view of a pressure applying mechanism applying pressure against the cranium parietally and obliquely, in accordance with one embodiment.
Figure 4D:
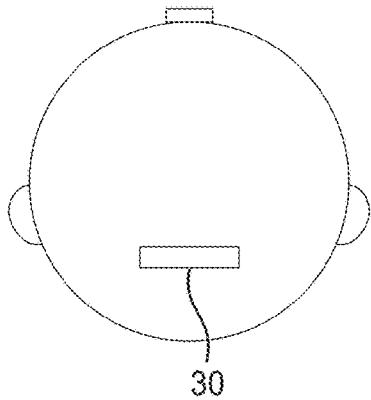
FIG. 4D is a top view of a pressure applying mechanism applying pressure against the cranium—with the head facing down-facing the infratentorial—cerebellar region, in accordance with one embodiment.
Figure 4E:
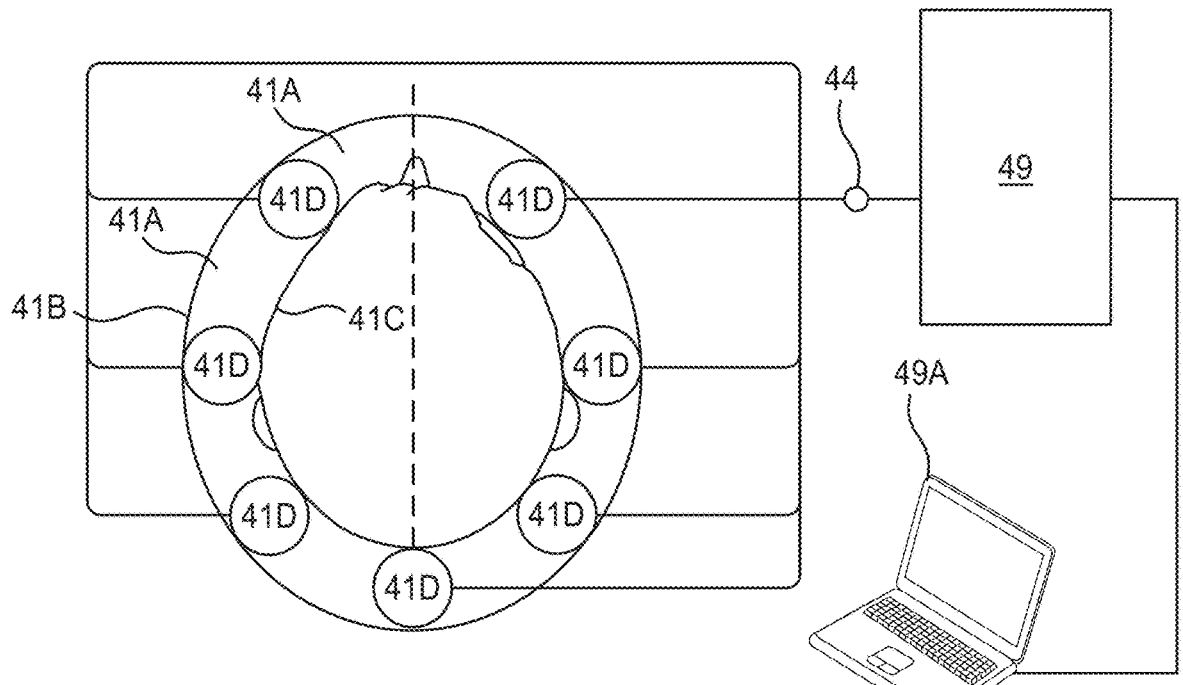
FIG. 4E is a view of a pressure applying mechanism applying pressure against the cranium temporally, occipitally, obliquely and parietally, in accordance with one embodiment.
Figure 4F:
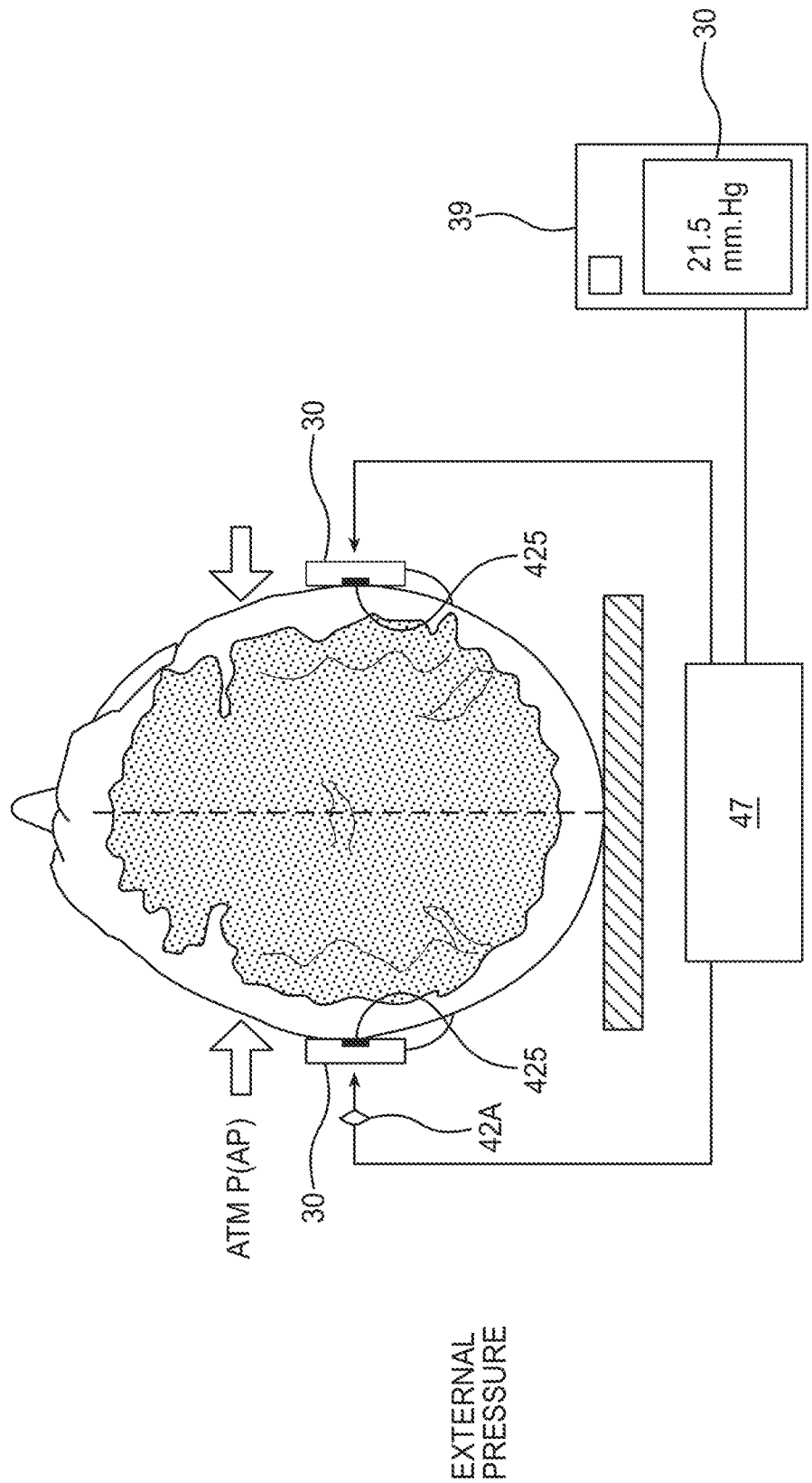
FIG. 4F is a top view of a pressure applying mechanism applying pressure against the cranium temporally and including a manometer, in accordance with one embodiment.

The pressure application instrument 30, in some embodiments, is configured to measure the externally applied pressure to the cranium using a manometer 39, as shown in FIG. 4F. In some embodiments, instrument 30 is configured in certain embodiments to apply an initial pressure and subsequent greater pressures in uniform stepwise increments to the subject's cranium. For example, in one particular non-limiting embodiment, an initial pressure of 1 mm Hg is first applied non-invasively, then a pressure of 2 mm Hg is applied, then 3 mm Hg, then 4 mm Hg, then 5 mm Hg, and this stepwise upward progression is continued until the predefined decline in variability of the intracranial brain tissue pulsation waveform is detected from the display visually by the human user, or more preferably automatically by the computer system when the special purpose software measures the variability of the waveform dynamically. The detection of the compression in the waveform to a predefined decline in variability is one or a combination of (i) a visual detection by the user and more preferably (ii) a predefined alert by the computer system according to quantitative criteria written into the software 55, for example special purpose software 55. The alert may be based on at least one of (i) the length of time interval (T) or (ii) an intracranial reserve space capacity or (iii) a determination or a suspicion of a medical condition. It may also be based on the amount of pressure applied by instrument 30.

The purpose of the incremental pressure elevations is to slowly reach and thereby determine that external pressure level at which the external pressure meets resistance from the intracranial pressure. Such resistance is indicated by the changes in the ICP waveform baseline and amplitude, for example by the baseline dropping, which drop in the baseline was later followed by a sharp upturn in the baseline, as for example shown in FIG. 6A. Accordingly, in certain embodiments of the systems and methods described herein, the external cranial pressure applied is not applied incrementally or gradually by instrument 30 but rather all at once. One way this can occur is when previously the threshold pressure level at which resistance has been met has already been determined (for example having already been determined by incremental pressure elevations) and now it is possible to apply the external cranial pressure all at once to the previously determined external cranial pressure.

The multi-dimensional probe 20 is a modified version of a standard USB compatible ultrasound probe, such as a modified version of the standard USB compatible probes manufactured by Interson Corporation of California. Probe 20 preferably should be modified in several ways, in accordance with some embodiments. First, as shown in FIG. 1C probe 20 has in some embodiments a mechanism for dispensing a gel. For example, probe 20 in some embodiments has an automatic gel dispenser 26 which may include a gel reservoir 28, a tube 26b for gel transfer, a micromotor/microengine 29 and an actuating mechanism such as a button 26a. Second, as shown in FIG. 1C, the distal end of the probe 20 is configured to grip the skull 11. For example, in some embodiments the distal end of probe 20 is concave and has a shape that is adjustable so as to conform to an outer surface of the skull 11 of the subject. In some embodiments, for example, one or more springs 27 (FIG. 1C) are situated behind and connected to each piezoelectric crystal 22—or group of crystals—of the crystal array 22 of the probe 20. Third, the probe 20 is a multi-frequency probe whose emitter and receiver have different frequencies. In one example, the emitter has a frequency of 0.5 to 2 MHz and the receiver has a frequency of 1 to 4 MHz which may be double the frequency of the emitter frequency in some embodiments.

Figure 3B:
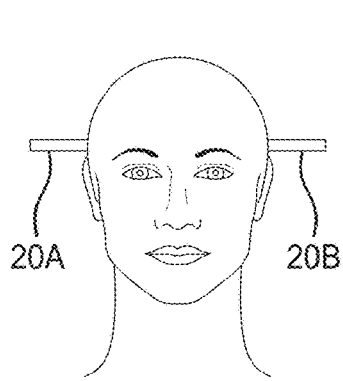
FIG. 3B is a schematic view of one mode of application of probe 20 to a subject's head where the receiver 20B is on the opposite of the head from the emitter 20A.
Figure 3C:
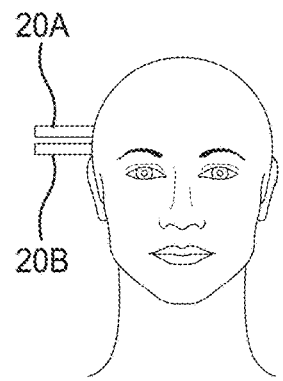
FIG. 3C is a schematic view of a second mode of application of probe 20 to a subject's head where receiver 20B is adjacent emitter 20A on the same side of the head.

In addition, in some embodiments shown in FIG. 3B the probe 20 has only a transmission mode having continuous voltage in which the emitter 20A of probe 20 is on one side of the head and the receiver 20B of probe 20 is on the opposite side of the head of the subject. In a different embodiment shown in FIG. 3C, probe 20 has both a continuous transmission mode (called "transmission mode") and a discrete transmission mode (called "impulse mode") which can be referred to as integrative mode in which the emitter and receiver of probe 20 are adjacent and preferably integrated into one device and applied to one side of the head. The impulse mode involves discrete non-continuous application of voltage. For example, as shown in FIG. 1B, a central section of the probe 20 having the central piezocrystal array 22 emits in transmission mode and the side (lateral) sections of the probe 20 having the side piezocrystal arrays 22A receiver at a different frequency and in impulse mode. This is also integrated into one device. The integrate mode is better because the signal to noise ratio is ratio is much higher and signals emitted are amplified. Since the different parts of the head are non-homogeneous and have different acoustic impedance, the border points between the materials of different impedance generate reflecting waves in different directions toward the receiver of the probe 20.

Probe 20 may be structured such that the electronics, which is heavy, is distanced by a connecting cable from the piezoelectric array of crystals to provide greater flexibility in use of the probe 20. The cable is grounded to block influence from an EMF field. In some embodiments, the two-dimensional probe 20 is a mechanical scanning probe that moves the emitters and receivers. The sector of the image generated by the probe 20 is shown in FIG. 3A. In another embodiment shown in FIG. 1B, static arrays of emitters and receivers having a shape that provides the sector is depicted. FIG. 1B shows both a central piezocystal array 22A and lateral piezocrystal arrays 24. The lateral piezocrystal arrays are also called side piezocrystal arrays. There is, in certain embodiments, as shown by FIG. 1B an angle between the central piezocrystal array 22A and the lateral piezocrystal arrays 24. This angle is 10 degrees on one side and 15-20 degrees on the second side, in some embodiments. This difference in angles provides greater versatility for probe 20 since skulls vary amongst humans.

As shown in FIG. 1Ca, as an alternative embodiment to that shown in FIG. 1C, springs 27 are situated on each horizontal end in order to maintain the piezoelectric crystals 22 that are at the ends of the crystals 22 facing the skull 11 of the subject (as opposed to the ends facing the springs 27). Since the skull 11 may vary from one person to another, each group of piezoelectric crystals other than the central group has a separate spring 27 adapted to cause the array of crystals to engage the skull 11.

In some embodiments, the ICP is also measured and the combination of parameters is used to determine medical decisions. For example, if the ICP is known to be low enough then it is recommended to measure and monitor ICRS.

Figure 1B:
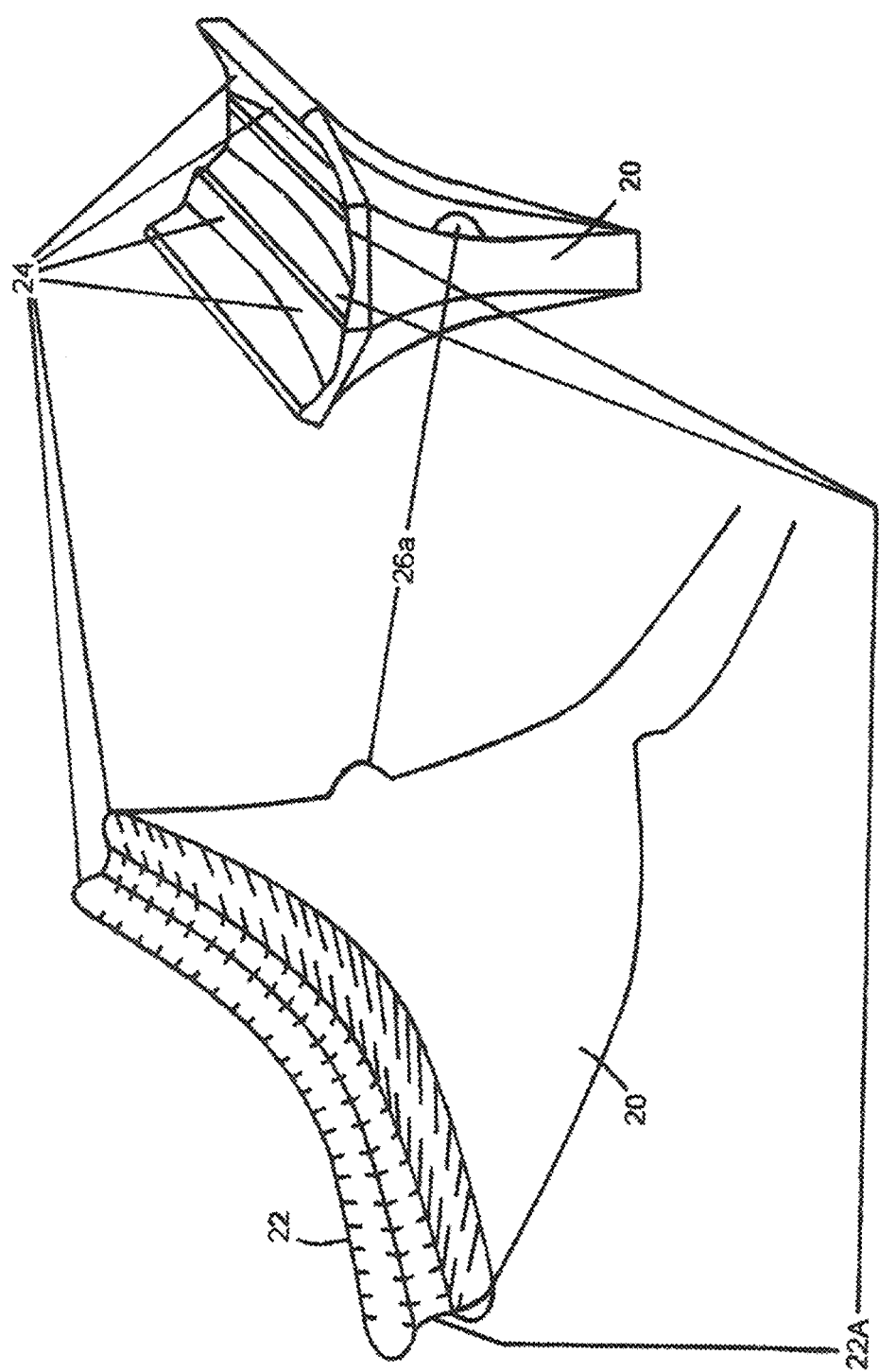
FIG. 1B is a perspective view of the ultrasound probe of FIG. 1A, in accordance with one embodiment.
Figure 1C:
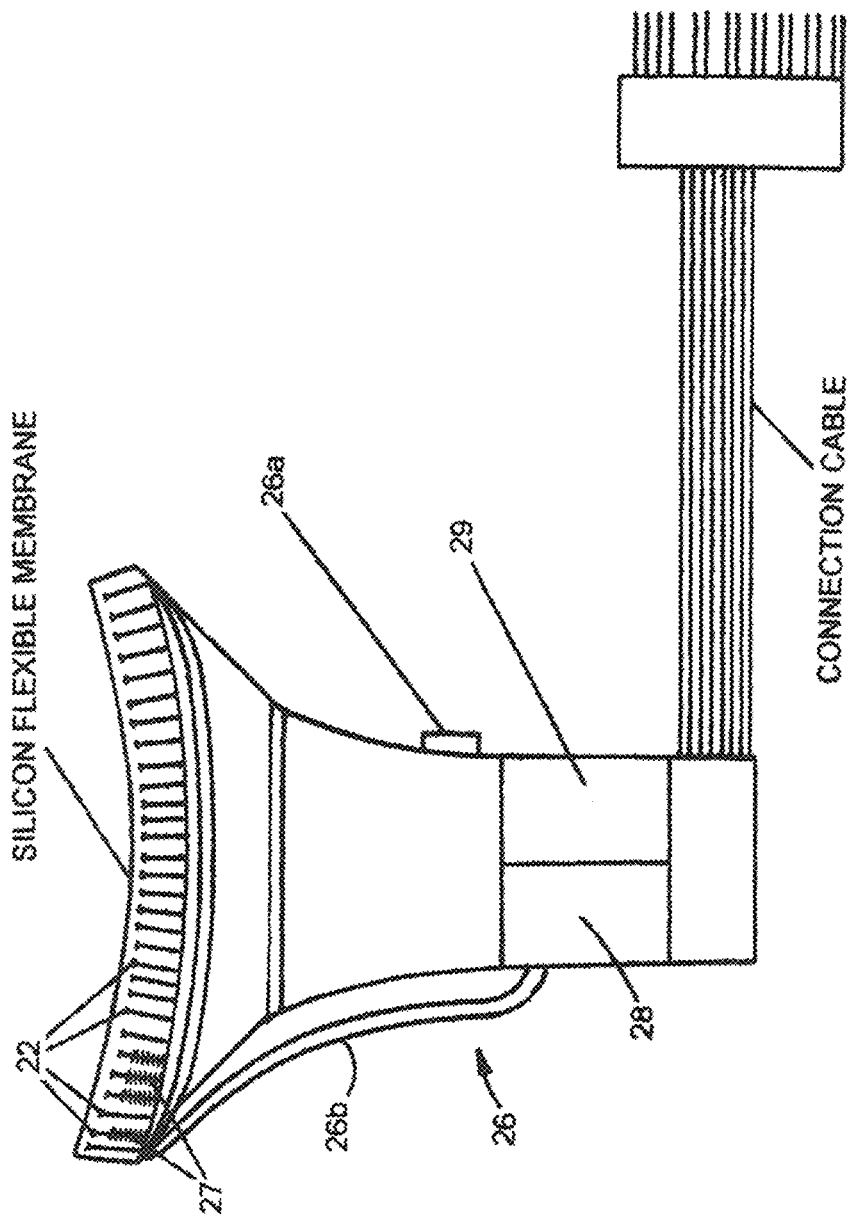
FIG. 1C is a lateral side view of the ultrasound probe of FIG. 1A, in accordance with one embodiment.
Figure 1C:
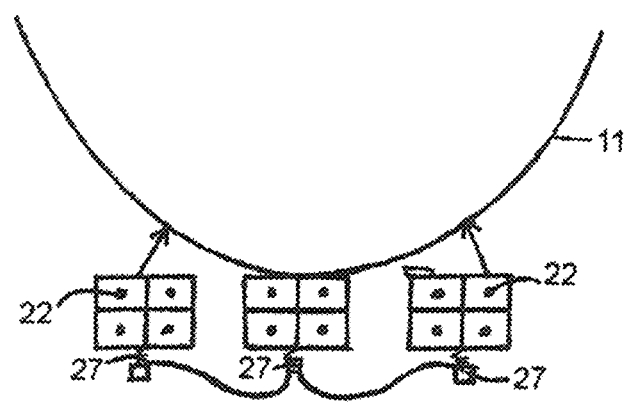

Referring now to FIGS. 1A through 1C, there are shown, by way of example, a novel ultrasound probe 20 used for intracranial space measurement in accordance with one or more embodiments described herein. In the embodiments shown in FIGS. 1A-1C, ultrasound probe 20 is designed to be adjustable to suit the curvature of the skull 11 surface, which varies from one individual to another. Thus optimal contact is assured, for best definition. The probe 20 has ultrasound multi frequencies and multi-axial mode. The probe is able to scan towards any spatial angle or dimensional axis (as compared to prior art single-dimensional probes). Additionally shown in FIG. 1C, the ultrasound probe 20 may include a gel reservoir 28, for example an acoustic gel reservoir, which may be mechanically activated to release and apply ultrasound gel upon the skull.

The central part of the probe, shown in FIG. 1B, includes 2D piezocrystals 22 with ultrasound carrier frequency of 0.8 MHz, and on the two sides of probe (receivers) with receiver frequency ranges from 1 MHz to 2 MHz, more preferably between 2 MHz and 4 MHz. By selecting successive subset of probes from the array, successive contiguous groups of probes and successive focal points, a series of pixels within the tissue may be observed which cover the entire volume of the tissue at a resolution dependent on the pixel size. In some embodiments, the probe is moved to various locations upon the skull, and optionally these sector scans are combined using relevant software, to obtain a scan inclusive of all anatomical regions of import. Certain embodiments described herein are thus equivalent to ultrasound computer tomography, without its disadvantages, such as that the claimed invention can be implemented dynamically and without harmful radiation.

As shown in FIG. 1B, ultrasound probe 20 in some embodiments is configured in a shape to be held adjacent a skull of the subject for example at the top of the head. In some embodiments, an adjustable flexible rectangular array 22 of ultrasound piezoelectric crystal array 22, for example including lateral piezoelectric arrays 24 and a central piezocrystal array 22A, as shown in FIG. 1B, is arranged in a custom-made array in which is brought in contact with the skull. An adjustable flexible rectangle array of ultrasound probes is arranged in a custom-made array 22 which is brought in contact with the surface of the skull more effectively.

In prior art ultrasound probes, the emitter and receiver typically operate within the same frequencies, and thus are unable to penetrate the skull at the typical frequencies (3-10 MHZ) used to view other human tissues. In contrast, in accordance with one particular embodiment, the emitter of probe 20 may emit at 0.5-3 MHZ while the receiver of probe 20 receives at approximately 1.0 MHz-6 MHz, which provides a high resolution scan. In accordance with one embodiment, the probe 20 uses a low frequency (0.5 MHz to 3.0 MHz, for example 0.8-2.6 MHZ, for example 1.7 MHz) ultrasound emitted signal as there is little attenuation of the skull at these frequencies. However, the receivers of probe 20 are high frequency receivers in the range of 1 MHz to 6 MHZ, more preferably between 1 to 4 MHz (which provides high resolution). In general, the emitting frequency is lower than the receiving frequency and in one embodiment both emitting and receiving frequencies are between 0.5 and 3.5 MHz. Typically, the receiving frequency is roughly twice the emitting frequency. In one particular embodiment, the ultrasound probe 20 emits at a frequency of about 0.5 MHz and receives at a frequency of 1.0 MHz. In one other particular embodiment, it emits at 1.76 and receives at 3.5 MHz. In one other particular embodiment, the ultrasound probe 20 emits at a frequency of about 1.0 MHz and receives at a frequency of up to about 1.7 to 1.8 MHZ, and in one embodiment 1.76 MHz, using a carrier emitter frequency of about 0.5 MHz to 1.8 MHz, and in particular an emitter frequency of 0.5 to 1.76 MHz.

As a result of the dual range frequency ultrasound probes, ultrasound power is less attenuated by bones through which the ultrasound waves travel. In addition, the visual spatial resolution of the brain tissue image is good. For example, in some embodiments the resolution of the ICP waveform (or waveform pattern) is more than 3000 points per cycle, for example more than 4000 points per cycle or more than 5000 points per cycle or more than 6000 points per cycle. This provides an advantage over the resolution achieved by the prior art, which is 3000 points per cycle. Reflected ultrasound energy from the tissue is received via the probes and then converted into output signals. A high resolution, fast processing unit will process these output signals from the probes, and determine the pulsatile activity and characterize the response status of the tissue target. This information is then transformed into quantitative measurements of tissue characteristics and intra tissue pressure.

As shown in FIG. 2A (see "focus point I" and "focus point II"), in some embodiments, multi-frequency ultrasound probe 20 is configured in some embodiments to receive ultrasound waves from at least two different intracranial locations. As shown in FIG. 2A, in some embodiment the two different intracranial locations are dissimilar according to predetermined criteria. The computer system 50 is configured in some embodiments to determine a representative ICRS parameter from separate respective ICRS magnitudes at the at least two different intracranial locations. In one embodiment, these two different locations are preferably unlike one another, for example one location could be a surface of the cranium and a second location could be the third ventricle (or tissue that is located between the surface of the cranium and the third ventricle). In one embodiment, when the user applies probe 20 to a first of the different locations, the user situates the probe 20 horizontally whereas when the user applies probe 20 to a second of the different locations, the user situates the probe 20 vertically. In another embodiment, when the user applies probe 20 to a first of the different locations, the user situates the probe 20 vertically whereas when the user applies probe 20 to a second of the different locations, the user situates the probe 20 horizontally. In either of these two embodiments, applying the probe 20 in both horizontal and vertical positions enhances the accuracy of the data obtained for the ICP waveform.

In some embodiments, computer system 50 is further configured to convert the signal received from probe 20 into a dynamic image of a pulsatility of brain tissue, and in particular a multiaxial pulsatility or a three-dimensional pulsatility of brain tissue, in at least a part of the head that the probe received ultrasound waves from. System 10 includes all hardware and software necessary to implement this, including in some embodiments, special purpose software configured to convert the signal into multi-dimensional brain tissue pulsations and to derive real time digital intracranial pressure waves. The multi-dimensional pulsations in some embodiments include all three mutually perpendicular planes for multiaxial directions including in some embodiments multiple oblique directions in each of the three mutually perpendicular planes. The dynamic image of brain tissue pulsatility is displayed on a computer display for the user to see. The image of brain tissue pulsatility is a continuous dynamic image in some embodiments. Some embodiments provide the possibility of fourfold magnification of the images of the brain pulsation, which makes it much easier to see very tiny pulsations of brain tissue. In some embodiments, this provides visualization in real time of the brain tissue moving in three dimensions, by means of special purpose software. This provides a visual display of the brain tissue to the physician, technician or user. However, even without this, in certain embodiments of the system or method, one is able to determine the length of the specially defined time interval (T) (for example ending when the variability of the ICP waveform has been compressed) and from this to calculate an additional ICRS parameter such as the overall general ICRS capacity or the local ICRS capacity. One can also determine whether the ICRS or local ICRS is normal, too large or too small.

As a result of the computer system 50, for example the processing unit 52, monitoring one or more intracranial reserve space parameters, and in some embodiments also the intracranial pressure, the computer system 50 is configured to send an alert that the ICRS is abnormal such that an action, such as a surgery is needed or such that clinical deterioration of the subject is either predicted to occur or inferred to have occurred based on an abnormal ICRS.

In certain embodiments, the computer system is further configured to determine a magnitude of an intracranial reserve space (ICRS) parameter. One such parameter is the length of a time interval defined from a particular starting point occurring after the external cranial pressure has commenced until the amplitude or other waveform parameter achieves a predefined level of variability decline, for example flattening out to a predefined percent of previous variability. This length of time parameter provides information as to whether the ICRS is normal, too large or too small, by inference. This determination of whether the ICRS is too small, normal or too large may consider the age of the subject and other suitable characteristics. In some embodiments, this determination considers the ICP of the subject, for example an ICP of the subject as determined by certain embodiments described herein.

The "ICRS capacity" corresponds to the available volume of intracranial reserve space that existed before the external pressure—by pushing the CSF out of the cranium into the spinal canal—until the brain tissue pulsations were compressed. This volume parameter, as well as the length of time it takes for the ICRS to be "occupied", are useful to neurosurgeons and others in making determinations as to the tentative diagnosis of the patient, what treatment to administer and the prognosis. In accordance with the certain embodiments of the system and method described herein, this parameter is non-invasively measured repeatedly, for example multiple times within a period of time of an hour or multiple times within X minutes, wherein X is 15, 30, 45, 60, 75, 90, 120, 150, 180, 200, 250, 300, 350, 400 or 500 or multiple times within X hours, wherein X is 0.1, 0.2, 0.3 . . . 0.9 or 1.0, 2, 3, 4, 5, 6, 7, 8, 9, 10, 11, 12, 18, 24, 36, or 48 or a greater number of hours, or daily or weekly or bi-weekly or monthly or bi-monthly or quarterly or semi-annually or annually or at greater intervals. The repeated measurements are at uniform intervals in some embodiments. In other embodiments, the repeated measurements are not at uniform intervals. The ICRS parameter (for example either length of time T or ICRS capacity) is measured dynamically in some embodiments. Each time the ICRS parameter is measured, the pressure applying instrument 30 is applied to the cranium of the patient again. The magnitude of this pressure applied is too small for it to be a danger to the patient.

In certain embodiments, after repeating the determination of the ICRS parameter one or more times, for example length of time interval (T), in certain embodiments, the computer system 50 makes a prediction as to whether clinical deterioration of the patient will occur. In certain embodiments, after repeating the determination of the ICRS parameter, for example length of time interval (T), in certain embodiments, the computer system 50 makes a prediction as to whether the patient will experience elevated ICP. In each case (prediction of clinical deterioration and/or prediction of elevated ICP) the prediction may include a level of certainty and/or a time by which the prediction is expected to occur. The level of certainty may be expressed in terms of probability or any other suitable format known in the art. Further, in some cases, the prediction only occurs after multiple instances of the determination of the ICRS parameter being repeated, or only after a predefined length of time elapses during which the potential prediction is repeated, wherein a "potential prediction" refers to an output of a prediction by computer system 50 that is not formalized into an official diagnostic prediction until a predefined length of time elapses during which the potential prediction is repeated.

Accordingly, in some embodiments, the computer system 50 is configured to predict for the mammalian subject, for example a human patient, at least one of (i) an elevated ICP of the subject and (ii) clinical deterioration of the subject, the prediction being derived from the ICRS parameter, wherein the ICRS parameter is at least one of (i) the length of time interval (T) and (ii) the intracranial reserve space (ICRS) capacity.

Accordingly, the computer system 50 of system 10 is configured in some embodiments to send an alert or to display a determination of an ICRS parameter, for example an absolute volume comprising or corresponding to the ICRS capacity.

One particular useful output for physicians and other health care professionals or assistants from certain embodiments of the system 10 is the absolute length of time interval (T), for example in seconds or milliseconds or any other unit. In certain embodiments the time interval (T) is defined to extend from an endpoint of a first decline of a baseline of the ICP waveform occurring after the external pressure is applied, the endpoint adjacent a sharp upturn of the baseline during the interval, the interval ending when either (A) an amplitude of the waveform has declined by a predefined amount (for example relative to the amplitude at a predefined point in time) or (B) the waveform is compressed so as to exhibit a predefined decline in variability. The referred to variability in the waveform may reflect one or more variability characteristics including: amplitude, an area under the curve, dominant frequency, direction of high frequency shift, a phase shift or a multiaxial spectroscopy of the waveform.

Figure 8:
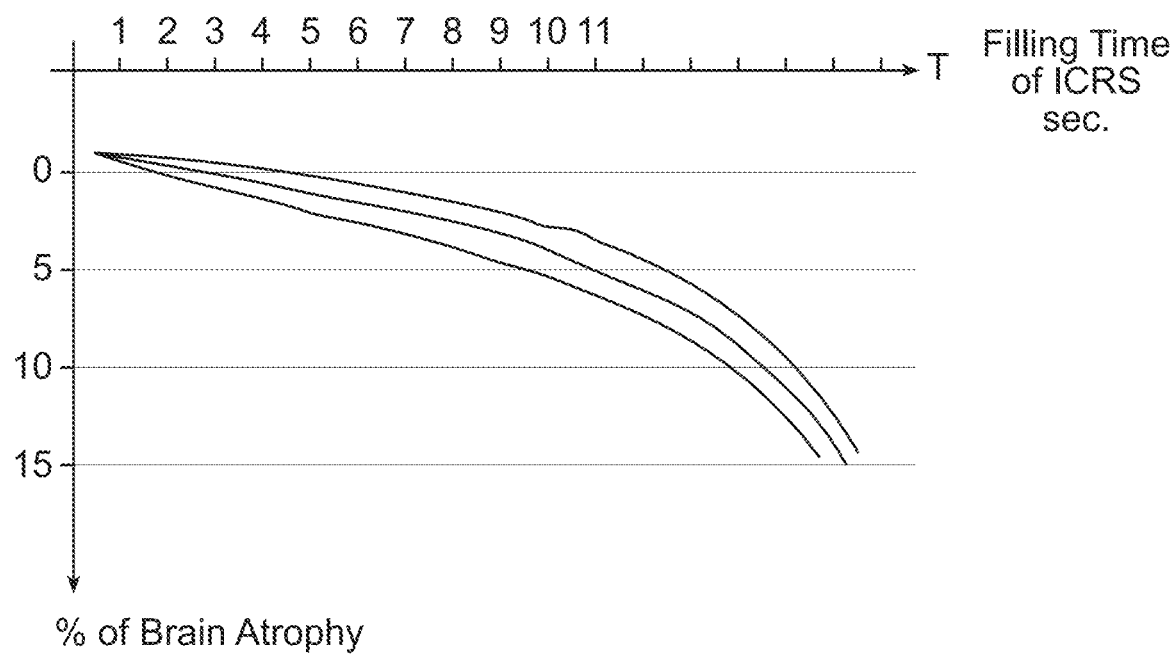
FIG. 8 is a graph of the relationship between the intracranial filling time interval (T) and a subject's brain atrophy, in accordance with one embodiment.

Another useful output for physicians and other health care professionals or assistants from certain embodiments of the system 10 is the relative length of time interval (T), for example in seconds or milliseconds, compared to a previous measurement, for example a recent measurement using certain embodiments. Another useful output for physicians and other health care professionals or assistants from the system 10 is a determination whether the length of time interval (T) is within a particular range of time, or in other embodiments is equal to a specific scalar time quantity, for example a time in seconds or milliseconds that is considered normal for a person's ICRS to become "occupied" upon commencement of the specially defined time interval that occurs after commencement of the external cranial pressure. This "normal" time may depend on the age of the individual. This "normal" time may depend on other characteristics of the individual, such as normality of ICP level and age. For example, many, although not all, elderly people experience atrophy of the brain tissue and this generates a larger space or ICRS (FIG. 8). Similarly, elevated ICP is associated with smaller ICRS. Accordingly, one is able to create handy physical charts or digital charts or look-up tables or other data that in some cases is provided to computer system 50 that provide the "normal" length of time expected for "occupying" the ICRS upon application of external cranial pressure based on one or more other parameters such as age, health including the existence of an intracranial growth, a pathology, ICP or another parameter. The "normal" times can be simple magnitudes or can be ranges of magnitudes, for example 3 to 5 seconds.

In some embodiments, the specific scalar normal time quantity is 2 seconds or 3 second or 2.5 seconds or anything between 2 and 3 seconds or another scalar time amount greater than 3 seconds or less than 2 seconds. The time represents the "normal" expected amount of time for the ICRS to become occupied as a result pf the external cranial pressure for a healthy person, possibly at a given age. This time would in some embodiments also take into consideration the amount of external pressure applied to the cranium, for example the pressure applied at the time the predefined amount of compression of the ICP waveform occurs. When compression is referred to, what is meant here is decline in variability of a waveform parameter to a predefined degree.

In one particular embodiment, as mentioned, the variability of the waveform characteristic, for example amplitude, is defined for example as a difference between the highest and lowest amplitude (or other characteristic) during a set cycle of say 10 milliseconds from on or after the initial external cranial pressure is applied, then in certain embodiments this is a reference point for an initial variability or for the variability at the first cycle. Then the variability of the ICP waveform during each subsequent time cycle, for example each subsequent 10 milliseconds, is monitored from when the external pressure commenced. Then, when the variability of the waveform has reached a predefined percentage lower than the original variability, the predefined amount of compression of the waveform has been deemed to have occurred and that represents the end time for purposes of measuring the specially defined length of time interval (T), one of the ICRS parameters used here in certain embodiments.

From the output of the intracranial reserve space parameter, which may be the length of time interval (T), the one or more processors of the computer system are configured in some cases to determine a suspicion or at least a suspicion or a tentative determination or a determination that clinical deterioration of the subject either occurred or is predicted to occur.

In some embodiments, the computer system, for example the one or more processors, is also configured to determine a "further length of time" beginning from the time at which the waveform is sufficiently compressed (i.e. the end of the time interval (T) so as to exhibit the predefined decline in variability and ending at a normalization time at which the predefined decline in variability has been reversed (brain tissue pulsation has been restored), the reversal such that a variability of the waveform at the normalization time equals, within a predefined degree of accuracy, a variability of the waveform at the start time. The normalization time has occurred when either (i) the amplitude of the ICP waveform returns to being equal to what it was at the start of the externally applied cranial pressure (i.e. equal to within a predefined level of accuracy) or (ii) the variability of the ICP waveform returns to be equal to what it was at the start of the externally applied cranial pressure, within a predefined level of accuracy. Note that the variability of the ICP waveform is measured using any of the same parameters used to measure the variability of the ICP waveform when determining the predefined decline in variability. The "further length of time" is defined as the time interval from the "subsequent time (T) at which the waveform is sufficiently compressed so as to exhibit a predefined decline in variability" until the "normalization time". The term "subsequent time" was used simply because it was subsequent to the start time of the length of time interval (T) used to measure the ICRS parameter. In some embodiments, the predefined level of accuracy is to within 5% and in other embodiments the predefined level of accuracy is to within 1% or 3% or 7% or 10% or 15% or 20% or 30% or 50% or a different percentage between 1% and 50%.

Accordingly, in some embodiments, the computer system 50 is configured to send an alert predicting future clinical deterioration of the subject if the further length of time is excessive or too short relative an expected normal further length of time. The expected "further length of time" for healthy individuals may vary depending on a number of factors but on average for adults it is approximately two to four seconds and about three seconds. In addition, the expected normal "further length of time" for normalization is in some embodiments determined based on what is expected normal for that particular patient from prior investigation of that patient rather than by comparing the particular patient to the population based on age or other factors.

Accordingly, in cases in which the ICRS parameter is found to be normal when checking a specific patient with a system or method described herein, if the "further length of time" to reach normalization, i.e. to restore brain tissue pulsation, is excessive or too short, the system 10 is configured in certain embodiments to send an alert. This alert in some embodiments predicts clinical deterioration of the patient. Since occupation of the ICRS has not yet occurred, the predicted future clinical deterioration is not immediate clinical deterioration but rather is more distant than "immediate, for example a day or two in the future. Thus, this further length of time is an even earlier predictor or marker for future clinical deterioration of a patient than the length of time until the ICRS is occupied.

In some embodiments, system 10 (FIG. 3A) may be configured for determining information (the presence of brain atrophy and if so the degree of brain atrophy) concerning a brain atrophy of a mammalian subject. System 10 may comprise:

an at least two-dimensional multi-frequency ultrasound probe 20 configured to emit and receive ultrasound waves into and from a head of the subject and to produce a signal of intracranial brain tissue pulsations in at least two of a horizontal (axial) spatial, a vertical (coronal) and a sagittal spatial dimension, the brain tissue pulsations responsive to pulses of a heart systole and/or respiration waves;

a pressure applicator mechanism 30, including at least one surface and a manometer, configured to non-invasively apply an external pressure to at least one of the locations $L_i$ of the skull of the subject using the at least one surface; and one or more processors 50 configured to
(I) receive the signal and at least one output of the external pressure from the pressure applicator mechanism,
(II) derive from the signal an intracranial brain tissue pulsation waveform and determine a length of an interval that starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount (relative to the amplitude at a predefined point in time) or (B) the waveform is compressed so as to exhibit a predefined decline in variability, and
(III) determine from the length of time of the interval a presence of and, if so, an amount or a degree of, the brain atrophy and output the determination.

In some embodiments, pressure applicator mechanism 30 is configured to apply external pressure to at least two of the following locations, $L_i$, of the cranium: (i) frontal, (ii) temporal, (iii) parietal, (iv) occipital using a surface adjacent the relevant location of the cranium. The one or more processors 50 are configured to determine a time interval (T) for filling each of the at least two locations, $L_i$, and to determine an intracranial location of the brain atrophy based on which time interval (T) is the longest time interval (T).

In some embodiments, the at least one of the locations, $L_i$, that probe 30 is configured to exert pressure against externally comprise at least two of or at least three of or all four of the following locations, $L_i$, of the cranium: (i) frontal, (ii) temporal, (iii) parietal, (iv) occipital, and further comprising using the one or more processors to determine the intracranial location of the brain atrophy based on which time interval (T) of the at least two of the locations, $L_i$, is longest.

In some embodiments, the determination of the intracranial location derives from a length of the period of filling of at least one of (i) a subarachnoid convexital space, (ii) a cerebral basal surface CSF shell and (iii) an intracerebral ventricular space (ICVS) and then comparing the time interval (T) for each to see which time interval is the longest.

In some versions, the one or more processors are configured to determine an amount of brain atrophy in the basal forebrain or left hippocampus.

In some embodiments, the time interval (T) includes a period of filling of a cerebral convexital subarachnoid space, a cerebral basal surface CSF shell and an intracerebral ventricular space (ICVS).

In some embodiments, system 10 or its components (probe 20 or computer system 50) is utilized in accordance with any of the steps or actions described below in relation to method 100.

Figure 9:
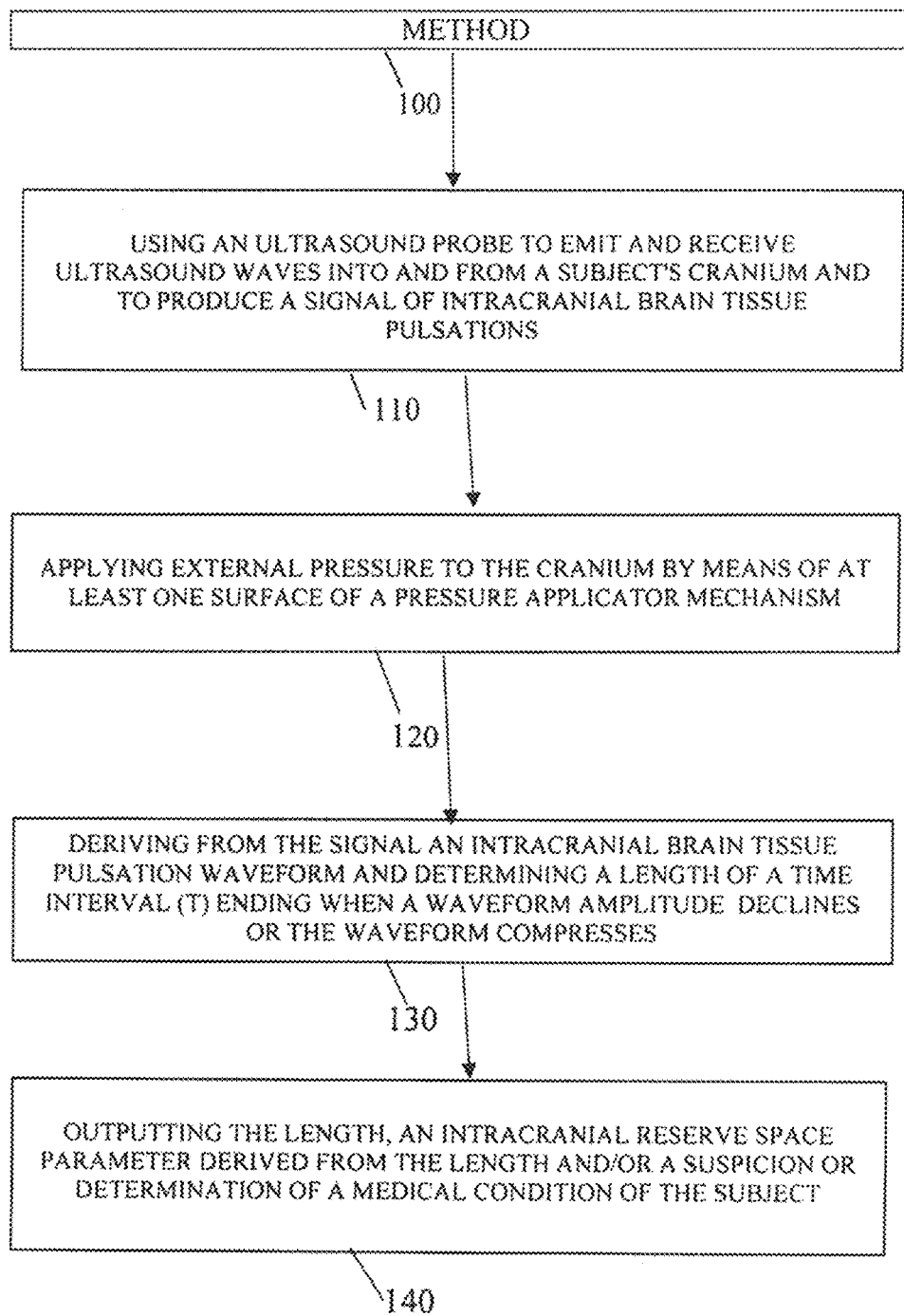
FIG. 9 is a flow chart showing a method in accordance with one embodiment.

As shown in FIG. 9, one embodiment is a method 100 of non-invasively monitoring an intra-cranial reserve space parameter of a mammalian subject, for example a general intracranial reserve space (ICRS). Unlike what is called "minimal intracranial reserve space", which comprises a convexital (superficial hemispheric) subarachnoid space (SHSS) and a basal surface subarachnoid space of the subject, general intracranial reserve space or "intracranial reserve space" without the qualifier "minimal" also includes the intracerebral ventricular space (ICVS).

Method 100 comprises a step 110 of using a probe to emit and receive ultrasound frequency waves into and from a body part, for example a head, of the subject during a time interval and to produce a signal corresponding to pulsation of brain tissue of the subject. The probe, in one embodiment, is a two-dimensional probe with a lower emitter frequency than the receiver frequency. For example, the emitter may emit at 0.5-3 MHZ while the receiver receives at approximately 1.0 MHz-6 MHz, which provides a high resolution scan. In some embodiments, the probe 20 has any of the characteristics mentioned in regard to probe 20 of system 10.

In one version, method step 100 comprises using an at least two-dimensional multi-frequency ultrasound probe configured to emit and receive ultrasound waves into and from a head of the subject and to produce a signal of intracranial brain tissue pulsations in at least a horizontal spatial and a vertical spatial dimension, the brain tissue pulsations responsive to pulses of a heart systole and/or respiration waves.

Method 100 may further comprise a step 120 of using a pressure applicator mechanism, including at least one surface and a manometer, to non-invasively apply an external pressure to a skull of the subject using the at least one surface.

Another step 130 of method 100 is using one or more processors to
(a) receive the signal and at least one output (for example at least the initial output) of the external pressure from the pressure applicator mechanism,
(b) derive from the signal an intracranial brain tissue pulsation waveform and determine a length of an interval that starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount (for example relative to the amplitude at a predefined point in time) or (B) the waveform is compressed so as to exhibit a predefined decline in variability, and
(c) output at least one of (i) the length, (ii) an intracranial reserve space parameter derived from the length and (iii) a suspected or determined medical condition of the subject derived from the length.

With respect to the predefined decline in variability, in certain embodiments of method 100, the variability of the waveform comprises at least one of the following parameters: (i) a variability of an amplitude of the waveform and (ii) a variability of an area under the curve of the waveform, (iii) a variability of a dominant frequency of the waveform, (iv) a direction of high frequency shift of the waveform, (v) a phase shift of the waveform and (vi) a variability of a multiaxial spectroscopy of the waveform. In another embodiment, variability of the intracranial brain tissue pulsation waveform comprises a variability of at least one of the following ICP waveform parameters: (i) an amplitude of the waveform and (ii) an area under the curve of the waveform, (iii) a dominant frequency of the waveform (for example a frequency between 0.1 and 35 MHz) and (iv) and (vi) a multiaxial spectroscopy of the waveform (ICPWMS). The spectroscopy referred to herein is a mechanical motion (pulsatility) spectroscopy, not a magnetic or electrical spectroscopy. Other functions that indicate variability of the ICP waveform are also within method 100, including but not necessarily limited to combinations and/or derivatives of the above six examples of ICP waveform variability indicia/parameters.

Method 100 may also include a step of determining, by the one or more processors, whether the length of time of the interval exceeds a threshold length of time. In some embodiments, method 100 also includes determining, by the one or more processors, (for example from a look-up table) which particular range of lengths of time of the interval the determined length of time fits into and to output a category of the particular range.

The predefined amount of the decline in amplitude may be defined relative to a beginning amplitude of the waveform occurring when the baseline stabilizes after the start point. The predefined amount of the decline in amplitude of the waveform may be defined relative to an amplitude of the waveform beginning after a filling of a minimal intracranial reserve space, the minimal ICRS comprising a cerebral convexital subarachnoid space and a basal surface CSF space, of the subject. In some embodiments, the predefined amount is the predefined amount is an amount and the amount is at least 10% or the predefined amount is a range and all data points in the range are at least 10%. In some embodiments, the predefined amount of the decline is an amount and the amount is at least 50% or the predefined amount is a range and all data points in the range are at least 50% (or at least 10% or at least 20% or at least 30% or at least 40% or at least some number between 10% and 50%).

The predefined amount of the decline in amplitude may be defined relative to a beginning amplitude of the waveform occurring when the baseline stabilizes after the endpoint. The predefined amount of the decline may be defined as an amount and the amount is at least 10% or the predefined amount is a range and all data points in the range are at least 10% and the declined may be defined relatiove to the beginning amplitude.

In some embodiments, the predefined amount of the decline in amplitude is defined relative to the amplitude of the waveform before the first decline of the baseline. In some versions, this predefined amount of the decline is defined to be reached when the amplitude is less, by a particular percentage, than a particular amplitude or an average amplitude, existing before the first decline of the baseline is less than X % of a particular amplitude or of an average amplitude existing before the first decline of the baseline, wherein X % is a percentage from 50% to 90%.

In some implementations of method 100, the one or more processors are also configured to determine, from the length of the time interval, an amount or a degree of a brain atrophy of the subject. The brain atrophy may be defined as a percentage of whole brain volume (WBV). In some embodiments, the one or more processors are configured to determine the amount of the brain atrophy from a look-up table or a mathematical function correlating the length of the time interval with an amount of the brain atrophy. The look-up table may include graph and may be defined broadly. The look-up table may be stored on memory 54 of the processing unit 52 or computer system 50. The memory 54 may also be external to the system 10 in certain embodiments.

In one implementation of method 100, the one or more processors are configured to determine an intracranial location of the brain atrophy of the subject. In one version, the determination of the intracranial location derives from a length of the period of filling of at least one of (i) a convexital subarachnoid space, (ii) a cerebral basal surface CSF shell space and (iii) intracerebral ventricular CSF space. By applying pressure to only one or only two (or only three) particular portions of the cranium, the amount of unhealthy elongation of the time interval of filling of the spaces in that particular portion of the cranium may be measured so as to determine if brain atrophy is found there.

For convenience the time interval (T) of the filing of the space in a particular location of the brain (for example an interval that starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount (for example relative to the amplitude at a predefined point in time) or (B) the waveform is compressed so as to exhibit a predefined decline in variability) is called TL, which means the time interval that relates to the filling of the space in location L (as opposed to the general ICRS time interval (T). As shown in FIG. 4A, FIG. 4B, FIG. 4C, FIG. 4D and FIG. 4E, the particular portions of the cranium referred to are those spaces that appear in one or more of the following portions of the cranium: frontal, temporal, parietal, occipital, infratentorial-cerebellar. In one embodiment, the one or more processors are configured to determine an amount of brain atrophy in a basal forebrain or in a left and right hippocampus.

In certain embodiments of method 100, the one or more processors are configured to determine a magnitude or existence of a basal forebrain atrophy and to determine/output a pre-symptomatic marker for Alzheimer's disease from the determination of a degree or existence of the basal forebrain atrophy. The degree may be measured in percentage terms.

Steps 110, 120, 130 of method 100 in some embodiments may be repeated dynamically at least once (for example after an interval of minutes or hours or a day or days). The results of the two or more measurements of the ICRS parameter are compared to determine if there has been a change in length of time (T) or a change in the ICRS capacity.

In some embodiments, there is a step of determining by means of one or more processors of the computer system 50 the ICRS (i.e. the ICRS capacity) divided by the intracranial pressure.

In some embodiments, there is step of converting the signal from the ultrasound probe applied of the head of the subject into a dynamic image of a pulsatility of brain tissue, wherein the image is of the sector of the head that the multi-frequency ultrasound probe received ultrasound waves from.

In some embodiments, there is a step of providing an output, to the physician or other user, of the ICRS parameter, for example the ICRS capacity, the length of time (T), and/or the ICRS capacity divided by intracranial pressure of the subject or another useful parameter and to provide such output dynamically and/or repeatedly, such as every minute or every 5 or 10 or 20 or 30 or 40 or 50 minutes or every hours or every several hours or every 3 or 4 or 5 or 6 or 9 or 12 hours or every day or every 2 or 3 or 3 or 4 or 5 or 7 or 10 days or every two weeks or every month. The computer system in some embodiments also determines that the subject has an abnormal intracranial reserve space and/or that clinical deterioration is either predicted to occur or inferred to have occurred.

Method 100 results in a length of time interval (T) having been determined. If this time interval is referred to as $(T_1)$, in some embodiments, method 100 may be repeated and a further or subsequent length of time $(T_2)$ may be determined.

In some embodiments, the method 100 is repeated and predicts at least one of (i) elevated ICP and (ii) clinical deterioration of the patient, if the subsequent length of time interval (T) is less than the length of time $(T_1)$ by a predefined amount (the term "amount" including both absolute amounts and relative amounts). The predefined amount can be a percentage or an absolute amount suitably determined based on age, medical condition and any other suitable factor. For example the predefined amount in some embodiments is a one-third decline or a 40% decline in the length of time, or 50%, or 60%, or 70%, or 80%, or 90%, or 100%, or a greater or lower percentage decline or some other numerical percentage between one-third and 100%, or a decline of at least a predefined absolute amount such as at least one half a second, at least three-quarters of a second, at least one second, at least 1.5 seconds at least 2 seconds, at least 2.5 seconds, at least 3 seconds or at least 3.5 or at least 4 seconds or any number in between 1 second and 4 second or greater than 4 seconds.

The method 100, or a variation thereof in which the ICRS parameter is the ICRS capacity rather than the length of time (T), may be performed and then repeated within a relative short interval dynamically with the results compared to determine if there has been a sudden or recent occupying of the ICRS.

The method 100 in some embodiments has any of the characteristics described in relation to system 10. For example, in some embodiments of method 100, the multi-frequency ultrasound probe 20 is configured to receive ultrasound waves from at least two different intracranial locations, as discussed in relation to system 10. In another example, in some embodiments, method 100 comprises sending an alert predicting at least one of (i) an elevated intracranial pressure and (ii) clinical deterioration of the subject, wherein the computer system may be configured to send the alert based on the length of time (T), the ICRS capacity and/or a given intracranial pressure applied. The following is an example of an experimental use of one aspect of a system and method described herein.

Figure 10:
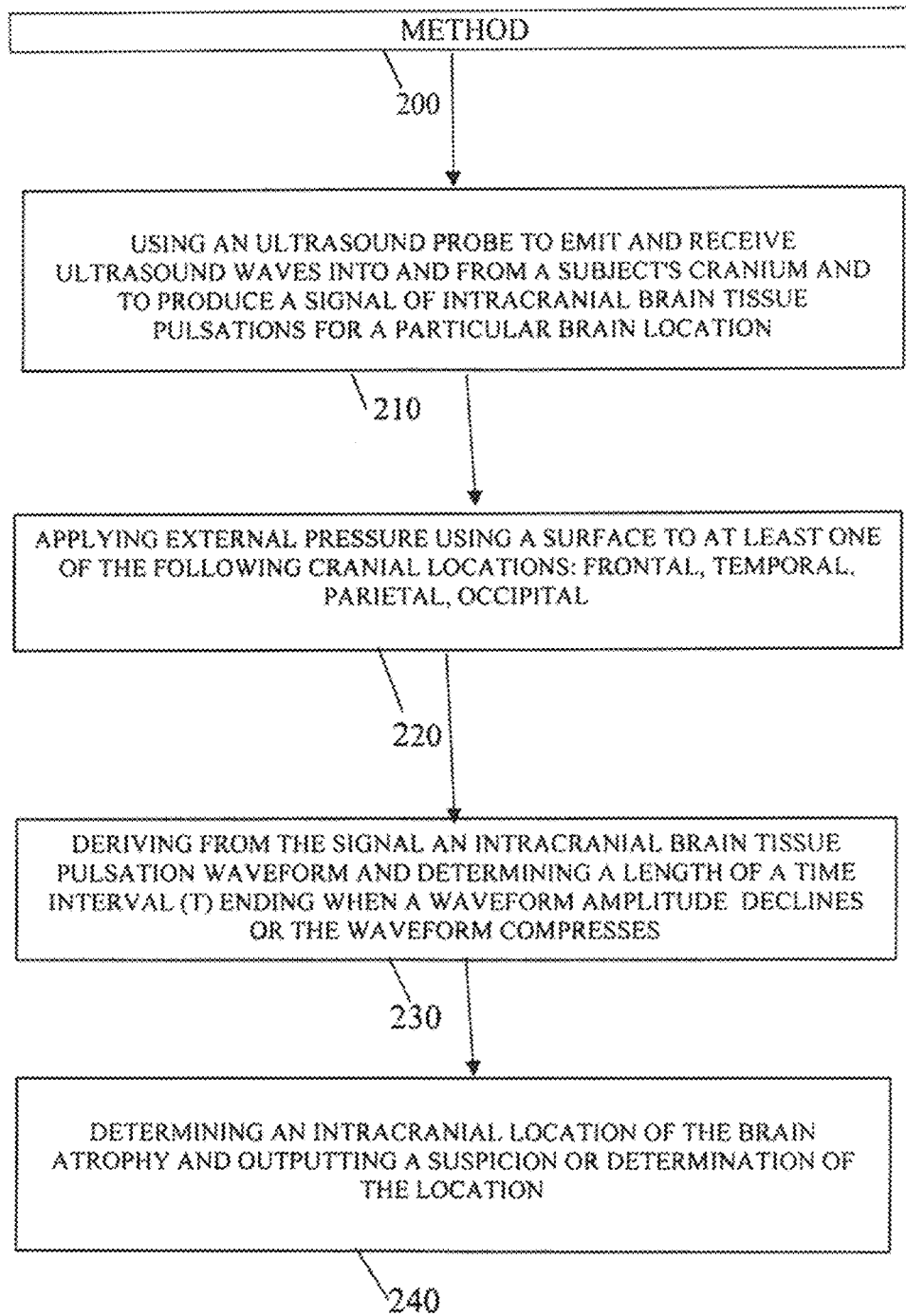
FIG. 10 is a flow chart showing a further method in accordance with one embodiment.

As shown in FIG. 10, another embodiment is a method 200 of non-invasively determining a location of brain atrophy of a mammalian subject. Method step 210 may comprise using an ultrasound probe to emit and receive ultrasound waves into and from a subject's cranium and to produce a signal of intracranial brain tissue pulsations for a particular brain location.

A second step 220 of method 200 comprises applying external pressure to the cranium at the brain location using at least one surface of a pressure applicator mechanism. The applicator mechanism may be any version described herein with respect to system 10 or method 100. This may be accomplished for example by applying the external pressure to at least one of or to at least two of or to at least three of or to all four of the following locations, $L_i$, of the cranium: (i) frontal, (ii) temporal, (iii) parietal, (iv) occipital. In one non-limiting implementation, the pressure application mechanism 30 is configured to apply pressure to multiple cranial locations by utilizing multiple surfaces or by being able to situate the at least one surface adjacent each of the (i) frontal, (ii) temporal, (iii) parietal, (iv) occipital portions of the cranium.

Method 200 may comprise a step 230 of using one or more processors to derive from the signal an intracranial brain tissue pulsation waveform and to determine a length of a time interval (T) of filling of an intracranial space at each of at least one of or at least two or at least three or all four of the particular cranial locations, $L_i$.

In some implementations, step 230 also comprises using one or more processors to derive from the signal an intracranial brain tissue pulsation waveform and to determine a length of a time interval (T), for example a length of an interval that starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount (for example relative to the amplitude at a predefined point in time) or (B) the waveform is compressed so as to exhibit a predefined decline in variability.

Method 200 may include a step 240 of using the one or more processors to determine an intracranial location of the brain atrophy.

In some versions, the at least one of the locations, $L_i$, comprises at least two of the locations, $L_i$, and method step 240 further comprises using the one or more processors to determine the intracranial location of the brain atrophy based on which time interval (T) of the at least two of the locations, $L_i$, is longest.

Method 200 may also comprise a step 250 of outputting a determination and/or a suspicion of the location of the subject's brain atrophy.

In some cases, method step 220 includes applying external pressure to the cranium to at least three of the following locations, $L_i$, of the cranium: (i) frontal, (ii) temporal, (iii) parietal, (iv) occipital (in some embodiments, a fifth location is a location of the cranium facing an infratentorial-cerebellar region of the brain), using the one or more processors to determine (A) the length of the time interval (T) of filling of the intracranial space at each of the at least three of the locations, $L_i$ and (B) the intracranial location of the brain atrophy based on which time interval (T) of the at least three of the locations, $L_i$, is longest.

The one or more processors 52 may be used to determine a time interval (T) for filling each of the at least two locations, $L_i$, and to determine an intracranial location of the brain atrophy based which time interval (T) for which of the at least two locations, $L_i$, is longest. The location of the brain atrophy is determined to be the location, $L_i$, whose time interval (T) is the longest.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A system for determining information concerning a brain atrophy of a mammalian subject, comprising:
   an at least two-dimensional multi-frequency ultrasound probe configured to emit and receive ultrasound waves into and from a head of the subject and to produce a signal of intracranial brain tissue pulsations in at least two of a horizontal (axial) spatial, a vertical (coronal) and a sagittal spatial dimension, the brain tissue pulsations responsive to pulses of a heart systole and/or respiration waves;
   a pressure applicator mechanism, including at least one surface and a manometer, configured to non-invasively apply an external pressure to at least one of the locations $L_i$ of the skull of the subject using the at least one surface; and
   one or more processors configured to
   receive the signal and at least one output of the external pressure from the pressure applicator mechanism,
   derive from the signal an intracranial brain tissue pulsation waveform and determine a length of an interval that starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount relative to the amplitude at a predefined point in time or (B) the waveform is compressed so as to exhibit a predefined decline in variability, and
   determine from the length of time of the interval a presence of and, if so, an amount or a degree of, the brain atrophy and output the determination,
   wherein the at least one of the locations, $L_i$, comprises at least two of the following locations, $L_i$, of the cranium: (i) frontal, (ii) temporal, (iii) parietal, (iv) occipital, and further comprising using the one or more processors to determine the intracranial location of the brain atrophy based on which time interval (T) of the at least two of the locations, $L_i$, is longest.

2. The system of claim 1, wherein the determination of the intracranial location derives from a length of the period of filling of at least one of (i) a subarachnoid convexital space, (ii) a cerebral basal surface CSF shell and (iii) an intracerebral ventricular space (ICVS).

3. The system of claim 1, wherein the one or more processors are configured to determine an amount of brain atrophy in the basal forebrain or left hippocampus.

4. The system of claim 1, wherein the interval includes a period of filling of a cerebral convexital subarachnoid space, a cerebral basal surface CSF shell and an intracerebral ventricular space (ICVS).

5. A system for determining information concerning a brain atrophy of a mammalian subject, comprising:
   an at least two-dimensional multi-frequency ultrasound probe configured to emit and receive ultrasound waves into and from a head of the subject and to produce a signal of intracranial brain tissue pulsations in at least two of a horizontal (axial) spatial, a vertical (coronal) and a sagittal spatial dimension, the brain tissue pulsations responsive to pulses of a heart systole and/or respiration waves;
   a pressure applicator mechanism, including at least one surface and a manometer, configured to non-invasively apply an external pressure to at least one of the locations $L_i$ of the skull of the subject using the at least one surface; and
   one or more processors configured to
   receive the signal and at least one output of the external pressure from the pressure applicator mechanism,
   derive from the signal an intracranial brain tissue pulsation waveform and determine a length of an interval that starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount relative to the amplitude at a predefined point in time or (B) the waveform is compressed so as to exhibit a predefined decline in variability, and
   determine from the length of time of the interval a presence of and, if so, an amount or a degree of, the brain atrophy and output the determination,
   wherein the pressure applicator mechanism is configured to apply external pressure to at least two of the following locations, $L_i$, of the cranium: (i) frontal, (ii) temporal, (iii) parietal, (iv) occipital and (v) infratentorial-cerebellar, and wherein the one or more processors is configured to determine a time interval (T) for filling each of the at least two locations, $L_i$, and to determine an intracranial location of the brain atrophy based on a longest time interval (T).

6. The system of claim 5, wherein the predefined amount is defined relative to a beginning amplitude of the waveform occurring when the baseline stabilizes after the start point.

7. The system of claim 5, wherein the predefined amount is defined relative to an amplitude of the waveform beginning after a filling of a minimal intracranial reserve space comprising a cerebral convexital subarachnoid space and a basal surface CSF shell of the subject.

8. The system of claim 5, wherein the predefined amount is an amount and the amount is at least 10% or the predefined amount is a range and all data points in the range are at least 10%.

9. The system of claim 5, wherein the amplitude at the predefined point in time is a beginning amplitude of the waveform occurring when the baseline stabilizes after the endpoint.

10. The system of claim 5, wherein the amplitude at the predefined point in time is the amplitude of the waveform before the first decline of the baseline.

11. The system of claim 10, wherein the predefined amount of the decline is defined to be reached when the amplitude is less than, by a particular percentage, a particular amplitude, or an average amplitude, existing before the first decline of the baseline.

12. The system of claim 5, wherein the one or more processors are also configured to determine, from the length of the time interval, an amount or a degree of a brain atrophy of the subject.

13. The system of claim 12, wherein the one or more processors are configured to determine the amount of the brain atrophy from a look-up table or a mathematical function correlating the length of the time interval with an amount of the brain atrophy.

14. The system of claim 12, wherein the one or more processors are configured to determine an intracranial location of the brain atrophy.

15. The system of claim 14, wherein the determination of the intracranial location derives from a length of the period of filling of at least one of (i) a convexital subarachnoid space, (ii) a cerebral basal surface CSF shell space and (iii) intracerebral ventricular CSF space.

16. The system of claim 5, wherein the one or more processors are configured to determine an amount of brain atrophy in a basal forebrain or in a left and right hippocampus.

17. The system of claim 5, wherein the interval includes a period of filling of a cerebral convexital subarachnoid space, a basal surface CSF shell space, cerebral basal cisterns and intracerebral ventricular spaces (ICVS).

18. The system of claim 5, wherein the one or more processors are configured to determine a magnitude or existence of a basal forebrain atrophy and to determine/output a presymptomatic marker for Alzheimer's disease from the determination of a degree or existence of the basal forebrain atrophy.

19. A method of non-invasively determining a location of a subject's brain atrophy, comprising:
   using an ultrasound probe to emit and receive ultrasound waves into and from the subject's cranium and to produce a signal of intracranial brain tissue pulsations for a particular brain location;
   applying external pressure using at least one surface to at least one of the following locations, $L_i$, of the cranium: (i) frontal, (ii) temporal, (iii) parietal, (iv) occipital;
   using one or more processors to derive from the signal an intracranial brain tissue pulsation waveform and to determine a length of a time interval (T) of filling of an intracranial space at each of the at least one of the locations, $L_i$;
   using the one or more processors to determine an intracranial location of the brain atrophy; and
   outputting a determination and/or a suspicion of the location of the subject's brain atrophy,
   wherein the at least one of the locations, $L_i$, comprises at least two of the locations, $L_i$, and further comprising using the one or more processors to determine the intracranial location of the brain atrophy based on which time interval (T) of the at least two of the locations, $L_i$, is longest.

20. The method of claim 19, further comprising applying external pressure to the cranium at three or more of the following locations, $L_i$, of the cranium: (i) frontal, (ii) temporal, (iii) parietal, (iv) occipital, using the one or more processors to determine (A) the length of the time interval (T) of filling of the intracranial space at each of the at least three of the locations, $L_i$ and (B) the intracranial location of the brain atrophy based on which time interval (T) of the at least three of the locations, $L_i$, is longest.

21. The method of claim 19, further comprising using the one or more processors to determine the time interval (T) such that the time interval starts at an endpoint of a first decline of a baseline of the waveform occurring after the external pressure is applied, the endpoint adjacent a sharp upturn of the baseline during the interval, the interval ending when either (A) an amplitude of the waveform has declined by a predefined amount or (B) the waveform is compressed so as to exhibit a predefined decline in variability.

\* \* \* \* \*